United States Patent
Centen et al.

(10) Patent No.: US 10,413,475 B2
(45) Date of Patent: Sep. 17, 2019

(54) WEARABLE CPR ASSIST, TRAINING AND TESTING DEVICE

(71) Applicant: Physio-Control, Inc., Redmond, WA (US)

(72) Inventors: Corey James Centen, Ottowa (CA); Nilesh Patel, Ontario (CA)

(73) Assignee: PHYSIO-CONTROL, INC., Redmond, WA (US)

( * ) Notice: Subject to any disclaimer, the term of this patent is extended or adjusted under 35 U.S.C. 154(b) by 40 days.

(21) Appl. No.: 14/691,466

(22) Filed: Apr. 20, 2015

(65) Prior Publication Data
US 2015/0224021 A1    Aug. 13, 2015

Related U.S. Application Data

(63) Continuation of application No. 11/936,184, filed on Nov. 7, 2007, now Pat. No. 9,028,259.
(Continued)

(51) Int. Cl.
*G09B 23/00* (2006.01)
*A61H 31/00* (2006.01)
*G09B 23/28* (2006.01)

(52) U.S. Cl.
CPC ......... *A61H 31/005* (2013.01); *G09B 23/288* (2013.01); *A61H 2201/5061* (2013.01);
(Continued)

(58) Field of Classification Search
CPC .... G09B 19/00; G09B 23/288; A61B 5/0205; A61H 31/004; A61H 31/005; Y10S 601/06
See application file for complete search history.

(56) References Cited

U.S. PATENT DOCUMENTS

| 4,048,991 A | 9/1977 | Marx |
| 4,092,788 A | 6/1978 | Gowing |

(Continued)

FOREIGN PATENT DOCUMENTS

| EP | 162616 | 11/1985 |
| WO | WO9839061 | 9/1998 |

OTHER PUBLICATIONS

Gruben, et al., System for Mechanical Measurements During Cardiopulmonary Resuscitation in Humans, 1990, IEEE Transactions on Biomedical Engineering, vol. 37, No. 2, pp. 204-210.
(Continued)

*Primary Examiner* — Peter Egloff
(74) *Attorney, Agent, or Firm* — Lane Powell PC

(57) ABSTRACT

A wearable cardiopulmonary resuscitation assist device or system including: a wearable article to be worn by a cardiopulmonary resuscitation performer or a patient, for assisting administration of cardiopulmonary resuscitation by the performer; at least one sensor for measuring at least one parameter to assist in cardiopulmonary resuscitation; at least one feedback component for conveying feedback information based on the parameter to the performer for assisting the performer in performing cardiopulmonary resuscitation; and a processing unit, the processing unit being configured to receive the at least one parameter from the at least one sensor and to send information based on the parameter to the at least one feedback component. Also a method for training or improving cardiopulmonary resuscitation procedures using the device.

24 Claims, 14 Drawing Sheets

Related U.S. Application Data

(60) Provisional application No. 60/880,228, filed on Jan. 16, 2007.

(52) U.S. Cl.
CPC ............... *A61H 2201/5064* (2013.01); *A61H 2201/5069* (2013.01); *A61H 2201/5084* (2013.01)

(56) References Cited

U.S. PATENT DOCUMENTS

| | | | |
|---|---|---|---|
| 4,405,171 A | 9/1983 | Payne et al. | |
| 4,645,251 A | 2/1987 | Jacobs | |
| 4,932,879 A | 6/1990 | Ingenito et al. | |
| 4,988,981 A | 1/1991 | Zimmerman et al. | |
| 5,088,037 A | 2/1992 | Battaglia | |
| 5,454,779 A | 10/1995 | Lurie et al. | |
| 5,468,151 A | 11/1995 | Egelandsdal et al. | |
| 5,496,257 A | 3/1996 | Kelly | |
| 5,588,919 A | 12/1996 | Nakamura | |
| 5,589,639 A | 12/1996 | D'Antonio et al. | |
| 5,645,522 A | 7/1997 | Lurie et al. | |
| 6,306,107 B1 | 10/2001 | Myklebust et al. | |
| 6,351,671 B1 | 2/2002 | Myklebust et al. | |
| 6,390,996 B1 | 5/2002 | Halperin et al. | |
| 6,551,252 B2 * | 4/2003 | Sackner | A61B 5/0205 600/536 |
| 6,676,613 B2 * | 1/2004 | Cantrell | A61H 31/00 601/41 |
| 6,681,003 B2 | 1/2004 | Linder et al. | |
| 6,690,969 B2 * | 2/2004 | Bystrom | A61H 31/005 128/897 |
| 6,827,695 B2 | 12/2004 | Palazzolo et al. | |
| 7,074,199 B2 | 7/2006 | Halperin et al. | |
| 7,108,665 B2 | 9/2006 | Halperin et al. | |
| 7,122,014 B2 | 10/2006 | Palazzolo et al. | |
| 7,220,235 B2 | 5/2007 | Geheb et al. | |
| 7,650,181 B2 | 1/2010 | Freeman et al. | |
| 2002/0193711 A1 | 12/2002 | Halperin et al. | |
| 2003/0036044 A1 | 2/2003 | Pastrick et al. | |
| 2003/0158593 A1 * | 8/2003 | Heilman | A61N 1/046 607/149 |
| 2005/0049515 A1 * | 3/2005 | Misczynski | A61B 5/0408 600/509 |
| 2006/0019229 A1 | 1/2006 | Morallee et al. | |
| 2006/0111749 A1 * | 5/2006 | Westenskow | A61M 16/00 607/5 |
| 2006/0117805 A1 * | 6/2006 | Valentine | A61B 5/0408 66/171 |
| 2007/0010764 A1 | 1/2007 | Palazzolo et al. | |
| 2007/0276300 A1 | 11/2007 | Olson et al. | |
| 2008/0312565 A1 | 12/2008 | Celik-Butler et al. | |
| 2010/0245114 A1 | 9/2010 | Celik-Butler et al. | |

OTHER PUBLICATIONS

Pinchak, et al., Accelerometer Measurements in CPR, 1984, 37th ACEMB, Los Angeles Hilton, p. 32.

Alfred C. Pinchak, et al., Chest Wall Acceleration and Force Measurements in Simulated Manual and Mechanical Cardiopulmonary Resuscitation, 1988, Critical Care Medicine, vol. 16, No. 2, pp. 151-160.

Aase, et al., Compression Depth Estimation for CPR Quality Assessment Using DSP on Accelerometer Signals, Mar. 2002, IEEE Transactions on Biomedical Engineering, vol. 49, No. 3, pp. 263-268.

http://www.analog.com/en/prod/0,,764_800_ADXL202,00.HTML, Feb. 23, 2007, downloaded from The Wayback Machine, May 14, 2019, 2 pp.

Atmel Corporation—Product Card, http://atmel.com/dyn/products/product_card_asp?part_id=2014.

Welcome—Linx Technologies offers wireless solutions with easily applied RF modules, antennas and connectors_ http://www.linxtechnologies.com.

FlexiForce®_ Load_Force Sensors and ELF_ Economical Load and Force System_http://www.tekscan.com/flexiforce.html.

* cited by examiner

WEARABLE CPR ASSIST, TRAINING AND TESTING DEVICE

CROSS-REFERENCE TO RELATED APPLICATIONS

This application is a continuation of co-pending U.S. application Ser. No. 13/188,412, filed Jul. 21, 2011, which is a continuation of Ser. No. 11/936,184, filed Nov. 7, 2007, which claims the benefit of U.S. Provisional Application No. 60/880,228, filed Jan. 16, 2007, the entirety of each of these applications is hereby incorporated by reference.

FIELD OF THE INVENTION

The present invention relates to CPR assist devices. In particular, the present invention relates to CPR assist devices that are wearable, and systems that include such devices.

BACKGROUND OF THE INVENTION

There are currently an estimated 40 000 incidences of cardiac arrest every year in Canada, most of which take place outside of hospital settings. The odds of an out-of-hospital cardiac arrest currently stand at approximately 5%. In the U.S., there are about 164 600 such instances each year, or about 0.55 per 1000 population. There is a desire to decrease these out-of-hospital incidences of cardiac arrest. Certain places, such as sports arenas, and certain individuals, such as the elderly, are at particular risk and in these places and, for these people, a convenient solution may be the difference between survival and death.

Cardiopulmonary resuscitation (CPR) is a proven effective technique for medical and non-medical professionals to improve the chance of survival for patients experiencing cardiac failure. CPR forces blood through the circulatory system until professional medical help arrives, thereby maintaining oxygen distribution throughout the patient's body. However, the quality of CPR is often poor. Retention of proper CPR technique and protocol may be inadequate in most individuals and the anxiety of an emergency situation may confuse and hinder an individual in delivering proper treatment.

According to the journal of the American Medical Association (2005), cardiopulmonary resuscitation (CPR) is often performed inconsistently and inefficiently, resulting in preventable deaths. Months after the completion of standard CPR training and testing, an individual's competency at performing effective chest compressions often deteriorates significantly. This finding was found to hold true for untrained performers as well as trained professionals such as paramedics, nurses, and even physicians.

The International Liaison Committee on Resuscitation in 2005 described an effective method of administering CPR and the parameters associated with an effective technique. Parameters include chest compression rate and chest compression depth. Chest compression rate is defined as the number of compression delivered per minute. Chest compression depth is defined as how far the patient's sternum is displaced. An effective compression rate may be 100 chest compressions per minute at a compression depth of about 4-5 cm. According to a 2005 study at Ulleval University Hospital in Norway, on average, compression rates were less than 90 compressions per minute and compression depth was too shallow for 37% of compressions.

According to the same study, CPR was often administered when unnecessary or was not administered when necessary. The study found that compressions were not delivered 48% of the time when cardiovascular circulation was absent.

Positioning of the hands is another parameter that may be considered when delivering CPR. It has been found that an effective position for the hands during compression is approximately 2 inches above the base of the sternum. Hand positioning for effective CPR may be different depending on the patient. For example, for performing CPR on an infant, an effective position may be to use two fingers over the sternum.

Other studies have found similar deficiencies in the delivery of CPR. One 2005 study at the University of Chicago found that 36.9% of the time, less than 80 compressions per minute where given, and 21.7% of the time, less than 70 compressions per minute were given. The chest compression rate was found to directly correlate to the spontaneous return of circulation after cardiac arrest.

In addition to too shallow compressions, too forceful compressions may also be problematic. Some injuries related to CPR are injury to the patient in the form of cracked ribs or cartilage separation. Such consequences may be due to excessive force or compression depth. Once again, lack of practice may be responsible for these injuries.

Therefore, a device to facilitate the proper delivery of CPR in an emergency is desired. Furthermore, a device that can also be used in objectively training and testing an individual may be useful for the CPR training process and protocol retention.

Current solutions in emergency cardiac care mostly focus on in-hospital treatment or appeal mostly to medical professionals. CPR assist devices that tether to defibrillators can be found in hospitals. However, these devices are often expensive and inaccessible to the lay individual who does not have a defibrillator on hand or cannot operate such a device. Furthermore, such devices are often not portable nor are they easily accessible. Simple devices with bar graph displays indicating compression force are often cumbersome in design and non-intuitive in use. Such a device may be uncomfortable to the patient and user and often has minimal data output. Thus, misuse of such a device is probable rendering it a hindrance rather than an aid.

There are currently mechanical systems for the delivery of CPR that may be used in a hospital setting. Chest compression may be delivered through a mechanism comprising mechanical movement (e.g., piston movement or motor movement). One such device is the AutoPulse™ by Revivant Corp, which has a computer-controlled motor attached to a wide chest band that compresses the chest, forcing blood to the brain when the heart has stopped beating.

Another device is the Q-CPR™ by Philips Medical, which is used to assess CPR quality. This device includes a CPR module connected to a defibrillation system. Although not currently marketed as a training device, the Q-CPR currently exists as a resuscitation aid and has future potential as a training technology. The device includes a block that provides compression depth and rate information to a rescuer through the display on the defibrillator. The CPR module is a unit placed on the patient's chest and under the hands of the individual performing the CPR. It may be cumbersome and may not be suited for use by non-medical professionals. The device has a multitude of instrumentation, which may make it expensive. In addition, the patient's comfort and safety may be a concern when an external, rigid device such as the Q-CPR is being employed. If the user is not familiar with the device, its use could result in injury.

Other devices, such the D-Padz™ by Zoll Medical employ similar technologies and thus encounter similar disadvantages.

The CPR-Ezy™ is a device that is independent from a defibrillator. It is a solid plastic block that is designed to be placed under the CPR performer's hands when performing CPR. Lights on its surface indicate the amount of force applied during a compression. Such a device may be bulky and awkward to use, and the feedback provided is limited and not quantitative. It also does not store information about the CPR performed.

Currently, a widely used technology in the training environment is the CPR mannequin. One commonly used version is the Resusci-Anne™ doll manufactured by Laerdal Medical Inc. The Resusci-Anne doll allows an individual to practice his or her CPR while being subjectively monitored by an instructor. This technique relies on the observational skills of the instructor and thus may be prone to human error. Furthermore, for effective training to take place, each student must be observed separately thereby occupying a significant amount of time and decreasing the number of students who can be trained at one time. In addition, Actar Airforce Inc. develops Actar™ mannequins providing limited feedback that are currently also used in CPR training. Again, such mannequins rely on close monitoring by the instructor to be effective for training.

Similar devices have also been disclosed, for example, in U.S. Pat. Nos. 7,220,235, 7,074,199, 6,351,671, and 5,468,151. Other CPR assist devices have been disclosed in U.S. Pat. Nos. 5,454,779, 5,645,522, US 2003/036044, U.S. Pat. No. 5,496,257, US 2006/019229, and EP 162616.

It would still be desirable to provide an easy-to-use and inexpensive device to provide instruction for carrying out a proper CPR procedure for training, testing, and/or emergency situations. Such a device may be intuitive to use.

SUMMARY OF THE INVENTION

An aspect of the present invention provides a wearable CPR assist device that may aid a performer in performing CPR. The device may also be inexpensive and/or adaptive. The device includes sensors for measuring various parameters during a CPR procedure, and may be used for training, testing, and/or real life emergencies. The device may provide instructions for performing CPR in the form of audio and/or visual feedback. The feedback may include information on parameters such as heart rate, compression rate, compression depth, compression force, compression angle, hand positioning, patient body temperature, patient body type, and patient blood oxygen content. The device may be accessible and usable to those trained and untrained in CPR.

The device may be in the form of an intuitive wearable article, to be worn by the performer or by the patient, allowing CPR to be administered as normal with no external devices necessary. By including all sensors in fixed positions on the device, the positioning of all sensors on the patient may be more likely to be accurate and precise. In some aspects, the sensors may be incorporated into a wearable glove to be worn by the performer for increased wearability and ease of use.

In some aspects, there is provided a wearable cardiopulmonary resuscitation assist device comprising: a wearable article to be worn by a cardiopulmonary resuscitation performer or a patient, for assisting administration of cardiopulmonary resuscitation by the performer; at least one sensor on the article for measuring at least one parameter to assist in cardiopulmonary resuscitation; at least one feedback component on the article for conveying feedback information based on the parameter to the performer for assisting the performer in performing cardiopulmonary resuscitation; and a processing unit on the article, the processing unit being configured to receive the at least one parameter from the at least one sensor and to send information based on the parameter to the at least one feedback component.

In some aspects, there is provided a system for assisting performance of cardiopulmonary resuscitation, the system comprising: a wearable cardiopulmonary resuscitation assist device, the device having: a wearable article to be worn by a cardiopulmonary resuscitation performer or a patient, for assisting administration of cardiopulmonary resuscitation by the performer; at least one sensor on the article for measuring at least one parameter to assist in cardiopulmonary resuscitation; and a base unit in communication with the device, the base unit having: at least one feedback component for conveying feedback information based on the at least one parameter to the performer for assisting the performer in performing cardiopulmonary resuscitation; and a processing unit configured to receive the at least one parameter from the at least one sensor and to send information based on the at least one parameter to the at least one feedback component.

In some aspects, there is provided a method of training a performer for cardiopulmonary resuscitation using a wearable cardiopulmonary resuscitation assist device, the method comprising: detecting at least one parameter for performing cardiopulmonary resuscitation using at least one sensor on the device; analyzing the at least one parameter compared to a desired cardiopulmonary resuscitation method; and providing feedback to the performer based on analysis of the at least one parameter.

In some aspects, there is provided a method of improving performance of cardiopulmonary resuscitation by a performer to a patient in need of such treatment, the method comprising: providing a wearable cardiopulmonary resuscitation assist device to be worn by the performer or the patient; detecting at least one parameter for performing cardiopulmonary resuscitation using at least one sensor on the device; analyzing the at least one parameter compared to a desired cardiopulmonary resuscitation method; and providing feedback to the performer based on analysis of the at least one parameter.

BRIEF DESCRIPTION OF THE DRAWINGS

Aspects of the present invention will be discussed in detail below, with reference to the drawings in which.

DETAILED DESCRIPTION OF THE INVENTION

The CPR assist device may be used to assist a CPR performer to carry out a CPR procedure on a patient. The device may also be used to train a CPR performer to properly perform CPR. The device may also be used to test whether a CPR performer is performing proper CPR. As such, although referred to as a CPR assist device, the device may be used not only for assisting in performance of CPR, but also or in the alternative be used for training or testing purposes. All examples and embodiments discussed in the present application are for purposes of illustration only and are not intended to be limiting.

The CPR assist device may include a wearable article containing the following basic components: a sensor and a feedback component. The device may also include a processing unit such as a microcontroller, and a power source or connection to a power source. Although the description and examples may refer to a microcontroller, the processing unit may be an analog circuitry, a microprocessor, or other suitable electronics. The device may also include a long-term memory, and data transmission means. These components will be described in greater detail in the respective sections below.

In some aspects, the CPR assist device is part of a system, and the CPR assist device may include a wearable article containing a sensor. The system may further include a base unit, the base unit having a feedback component and a processing unit. The base unit and the CPR assist device may be in communication, such that parameters sensed by the device or other related data may be communicated to the base unit, and the base unit then performs any necessary analysis of the parameter or data and conveys the result to the performer via the feedback component. The base unit may contain other components or modules for other functions, as will be discussed below.

The CPR assist device will be first discussed independent of the base unit, and later will be discussed as part of a system including the base unit.

Figure 1:
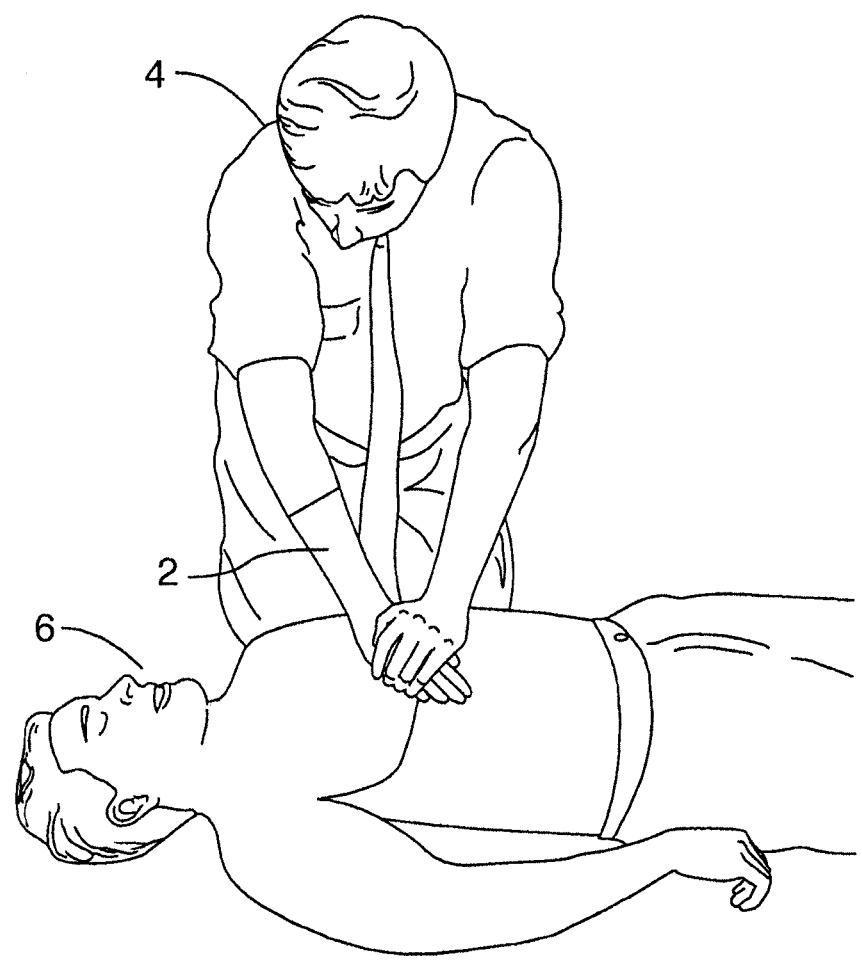
FIG. 1 is an illustration of a CPR assist device in the form of a CPR assist glove being used to perform CPR.

In some aspects, the CPR assist device is in the form of a CPR assist glove, as shown in FIG. 1. The CPR assist glove 2 may be worn by a CPR performer 4, to assist in providing CPR to a patient 6. The CPR assist glove 2 as shown is only one non-limiting example of the CPR assist device. Variations to the device are possible, as will be discussed below.

Figure 2:
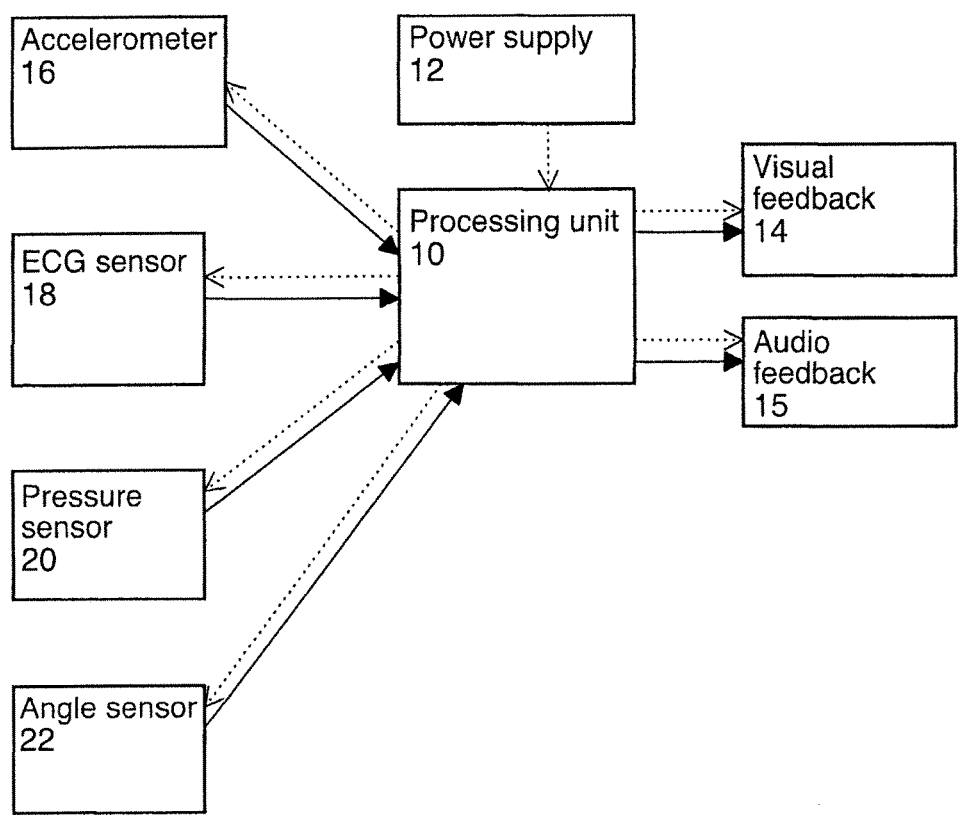
FIG. 2 is a block diagram illustrating an overview of a CPR assist system.

FIG. 2 is a block diagram showing an overview of the connectivity between the different components described above in an aspect of the device, where the device is to be used independent of the base unit. In the example shown, the device includes a processing unit (e.g., a microcontroller), a power source, at least one sensor, and at least one feedback component. The dashed arrows indicate the flow of power while the solid arrows indicate the flow of data. The processing unit 10 receives power from a power source 12 and delivers the power to at least one feedback component which may include a visual feedback 14 and an audio feedback 15, and at least one sensor which may include an accelerometer 16, an electrocardiogram (ECG) sensor 18, a pressure sensor 20, and an angle sensor 22. Data from each sensor 16, 18, 20, 22 is sent to the processing unit 10, which performs any necessary processing and analysis, and sends the processed or analyzed data to the feedback components 14, 15 for conveying to the performer. Although the above description is with reference to the device being used independent of a base unit, the components and the power and/or data flow may be similar where a base unit is used. Where a base unit is used, some components may be found on the base unit instead of the device, but the power and/or data flow may not be affected by this difference.

The CPR assist device may be in the form of any wearable article incorporating these components. The device may be configured to allow the sensors to pick up the patient information by directly contacting the patient, or by other direct or indirect methods. In some aspects, the sensors are configured to be brought into close proximity with the patient during CPR. By this is meant that the sensors may be brought up against the patient, though not necessarily in direct skin contact.

In some aspects, the CPR assist device is in the form of a glove that may be worn by the CPR performer, which will be referred to here as a CPR assist glove or simply a glove. Although this description may refer to the CPR assist device as being in the form of a glove, a person skilled in the art would understand that other wearable forms are possible that still provide the functions described herein.

Because the CPR assist device is wearable, it may be adaptable to situations in which an unwieldy device may be undesirable, for example in performing CPR on a small infant.

Wearable Article

The CPR assist device may be wearable by the performer or by the patient, and the wearable article may be adapted accordingly. In some aspects, the CPR assist device includes a glove as the wearable article, and is referred to as a CPR assist glove. Other possibilities for the wearable article may include a palm strap, a wrist strap, a partial glove, a vest, a watch, a ring, a bracelet, a belt, a mitten, or other similar articles. The wearable article may be of a suitable size and configuration to contain all the components of the device. In some aspects, the wearable article may be configured to allow at least one sensor housed in the wearable article to come into close proximity with the patient. Where the wearable article is to be worn by the patient, the wearable article may be adapted so that it can be easily put on the patient by the performer. This may be by making the wearable article to be widely adjustable, such as by providing Velcro™ straps or zippers.

The various components described above may be housed in separate compartments on the wearable article. The compartments for each component may be interchangeable, or more than one component may share one compartment. Some components may be more effective when housed in certain positions or in certain compartments, for example pressure sensors may be more effective located on the palm of the performer. These compartments may be padded to protect the components and the device may be made from a material that is easily cleaned and resistant to water and stain damage. The material of the wearable article may be a fabric material that can be stretched or otherwise adjusted (e.g., with a buckle or strap) to fit differently-sized performers. In some aspects, the various components may be removable from the device and the wearable article portion may be easily replaced or cleaned. This may allow for a sterile device each time CPR is performed. In another aspect of the invention, the device may have an outer layer that is at least water-resistant and that can be cleaned or disposed of after use. This outer layer may protect the device inside and the device components from contamination, and may eliminate or decrease concerns related to health or disease transmission. In some aspects, the wearable article may be made with sterile or sterilizable materials such as plastics. For example, in the case of a CPR assist glove, the glove may be a plastic shell that may be easily cleaned and sterilized.

Figure 3:
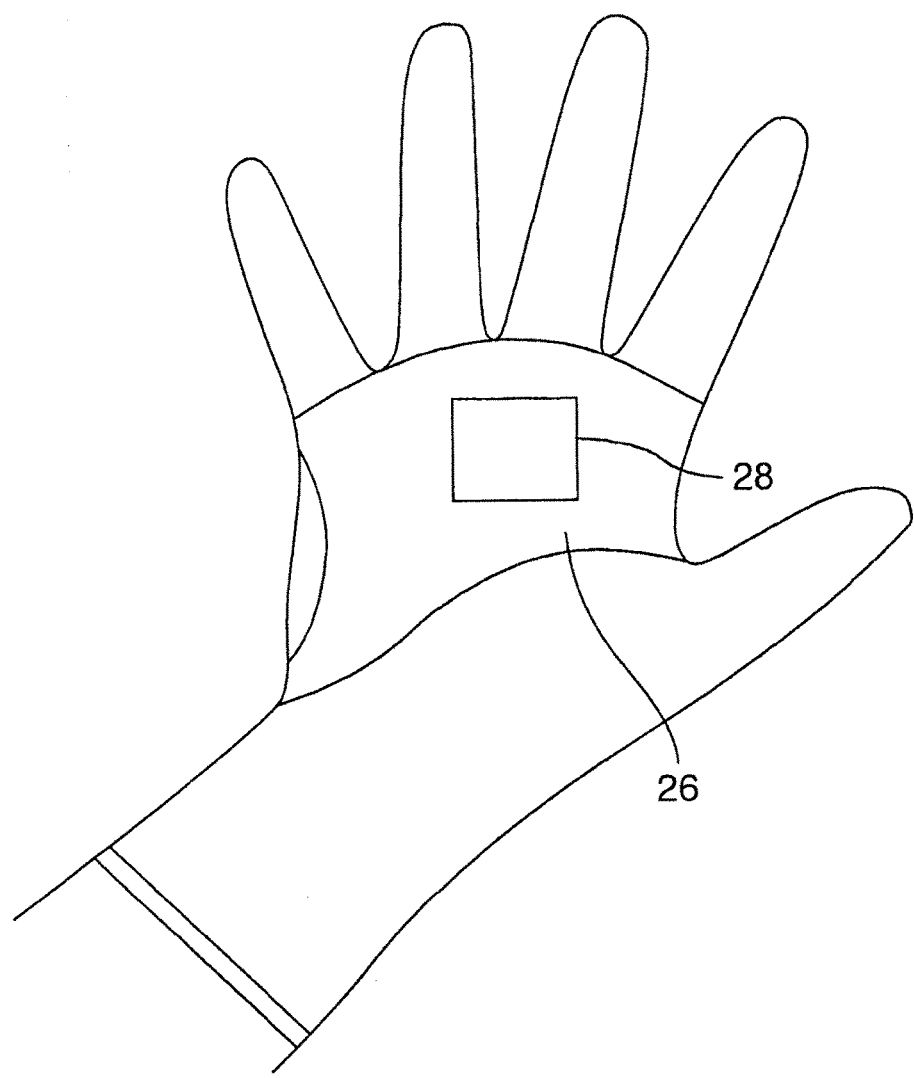
FIG. 3 is a top plan view of a CPR assist glove.
Figure 4:
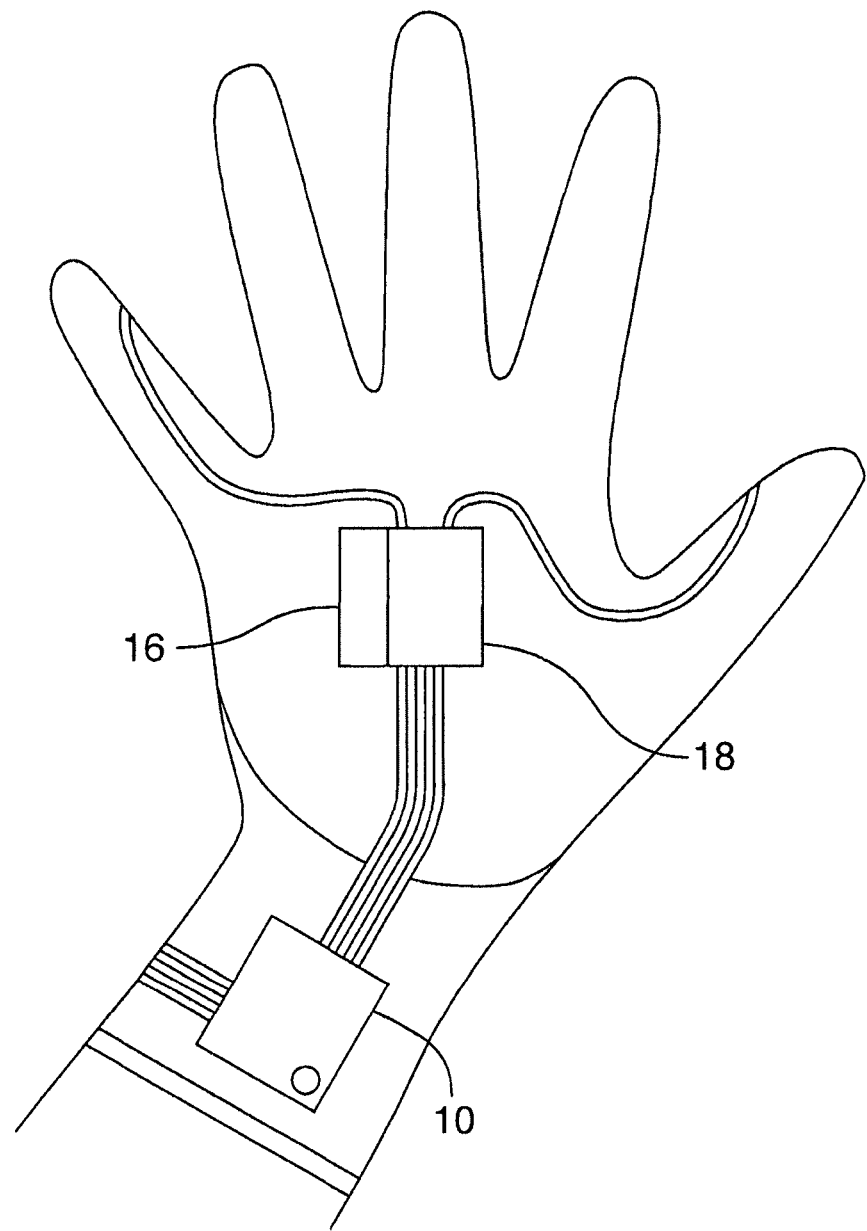
FIG. 4 is a top plan cutaway view showing components inside of the CPR assist glove of FIG. 2.
Figure 5:
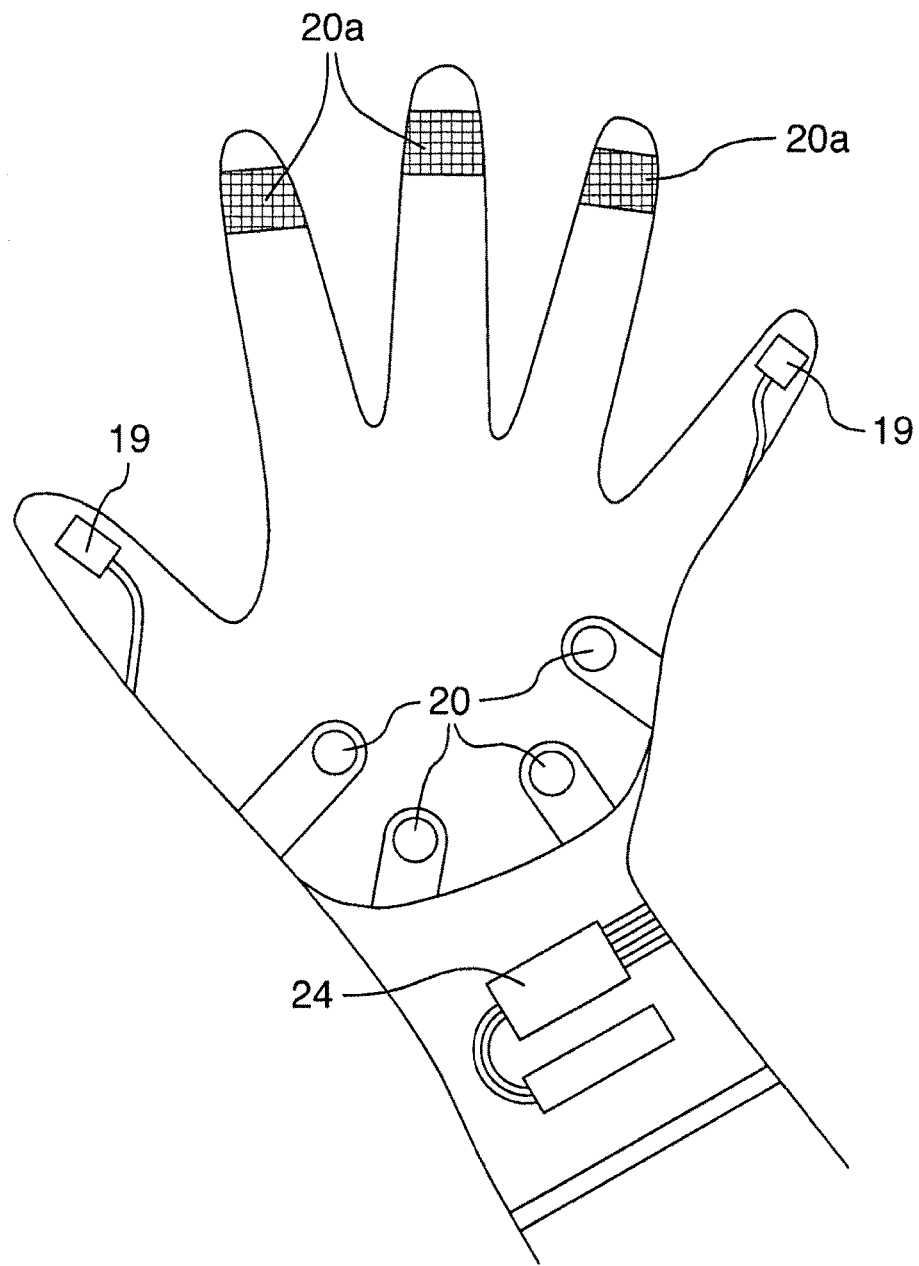
FIG. 5 is a bottom plan cutaway view showing components inside of the CPR assist glove of FIG. 2.

One example of the device in the form of a CPR assist glove is shown in FIGS. 3-5. FIGS. 3 and 4 show the glove from a top plan view (i.e., corresponding to the back of the hand), the latter being a cutaway view showing the components inside of the glove. FIG. 5 shows the inside of the glove from the bottom plan view (i.e., corresponding to the palm of the hand). The example shown includes three types of sensors: an electrocardiogram (ECG) sensor 18 with electrodes 19, an accelerometer 16, and pressure sensors 20. Other types of sensors may be included. The ECG sensor 18 may be located on the top of the glove (i.e., corresponding to the back of the hand) as shown, and may be connected to two electrodes 19 located on two opposing fingertips. The electrodes are illustrated here as being located on the pads of the thumb and the last finger, however other locations for the electrodes are possible (e.g., on other fingers or located on the palm), and more than two electrodes may be used. The accelerometer 16 may be housed along the lateral side of the hand opposite the thumb or on the top of the glove as shown. The accelerometer 16 does not need to be in contact with the patient, and thus may be located on the side or on the top of the glove. There may be four pressure sensors 20 located on the corners of the palm. Other configurations for the pressure sensors are possible, and there may be more or less than four pressure sensors 20. A processing unit 10 may be positioned on the superior side of the arm, just below the wrist. A power source 24 may be positioned on the opposite side of the arm, just below the wrist. The example CPR assist glove is also shown with additional pressure sensors 20a located on the fingertips. These additional pressure sensors 20a may be used where CPR is performed on an infant, in which case it may be desirable to have pressure sensors on the fingertips.

The location of these components may vary depending on what suits an individual performer and may be modified for different CPR efficiency and performer comfort. This layout may be different if different sensors were used, or if additional components were added. Certain sensors may be better located in certain positions, for example ECG sensors may be better located on the bottom side of the glove in order to come into close proximity with the patient. The configuration may be similar or different when used in a wearable article other than a glove. For example, in the case where the wearable article is a palm strap, the ECG sensors may be located on the palm rather than on the fingers.

Other aspects that are not shown may include a feedback component such as a display, for example a liquid crystal display (LCD). Other types of feedback components are discussed further below. The feedback component may be connected to the device or may be connected to a separate computing device, such as a computer, a base unit, or a receiving station, that may receive information from the device. Data may be transmitted to a separate computing device running software that may analyze and/or interpret the sensed data. Transmission of data may be by wired transmission or wirelessly using a transmission module in the device. The transmission module may be part of the processing unit, as described further below.

Although one layout of the components on a CPR assist glove is shown in the Figures, the layout may be different. For example, as already discussed, to allow for accurate and efficient infant CPR, the CPR assist glove may additionally or alternatively have sensors located in the fingertips of the glove to allow for two-finger CPR to a newborn infant. For example, pressure sensors on the fingertips may allow for determination of compression force during infant CPR. Other layouts may be suitable for different sensors and different applications. Infant CPR may also be measured using other sensors at other locations, for example, using an accelerometer located on the back of the hand for measuring compression depth, measurements of the performer's hand position can be made in the Z-axis (i.e., up-down direction).

In some aspects where the CPR assist device is in the form of a glove, there may be a wrist support added to the glove that may help someone with a weaker wrist or an ailment such as arthritis provide solid CPR. Furthermore, such a support may help improve the endurance of a performer during CPR and reduce ill-effects to the performer's wrist. The support may also serve to encourage effective CPR form by positioning the superior side of the hand (i.e. the back of the hand) perpendicular to the arm.

As shown in FIG. 3, the CPR assist glove may also have a sleeve 26 on top of the top side of the glove to help the performer position his or her second hand above the hand wearing the glove. This sleeve 26 may also contain sensors or other circuitry. This sleeve 26 may also be a convenient place to provide a display 28 for visual feedback to the performer or to provide selection choices (e.g., via a displayed menu) for the performer.

Figure 6:
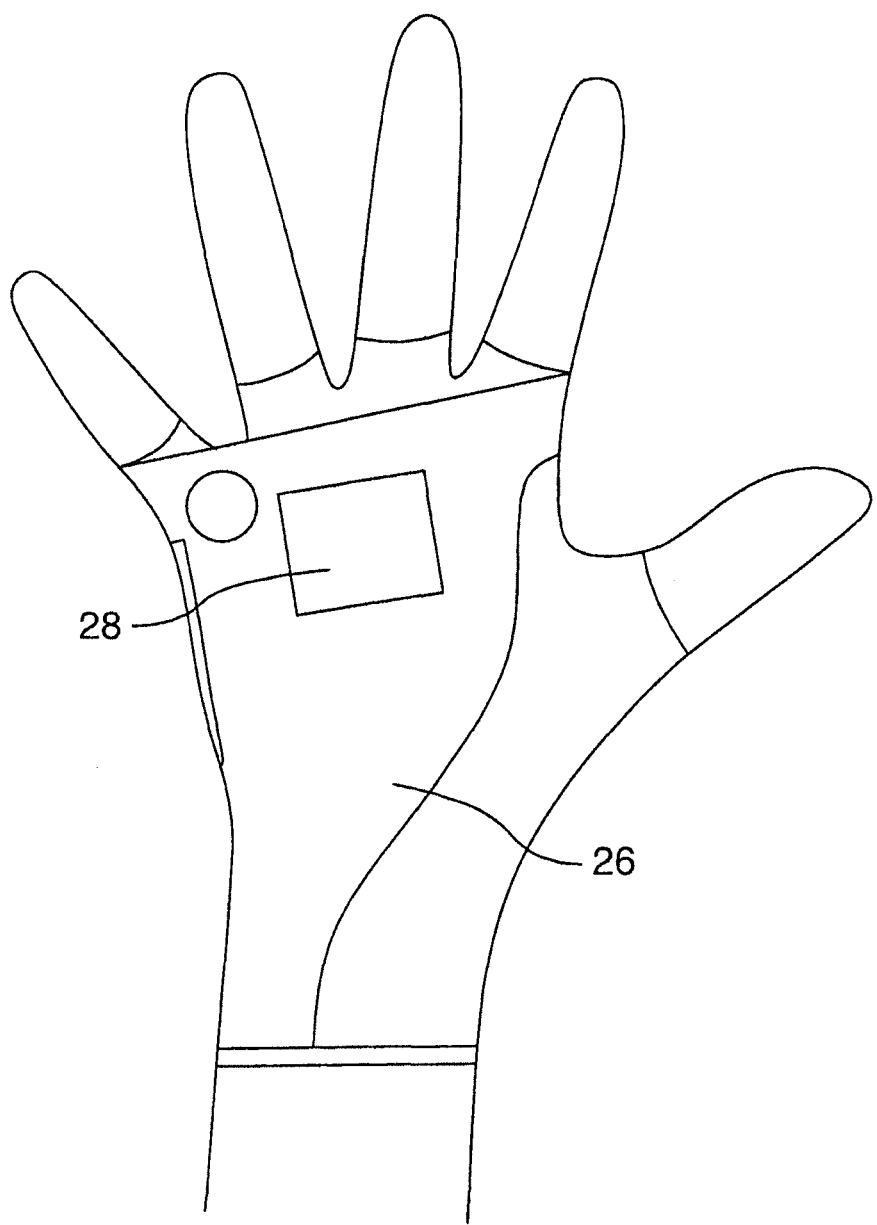
FIG. 6 is a top plan view of a fingerless CPR assist glove.
Figure 7:
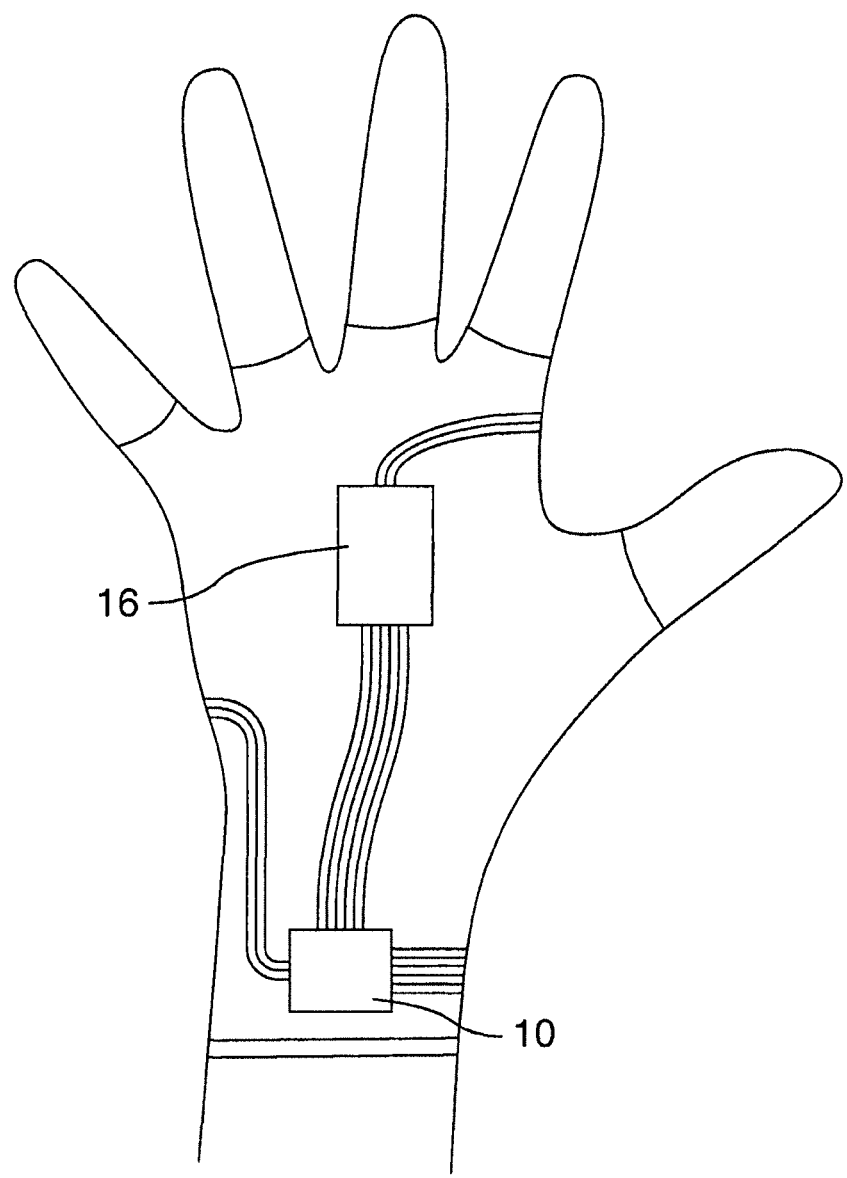
FIG. 7 is a top plan cutaway view showing components inside of the fingerless CPR assist glove of FIG. 5.
Figure 8:
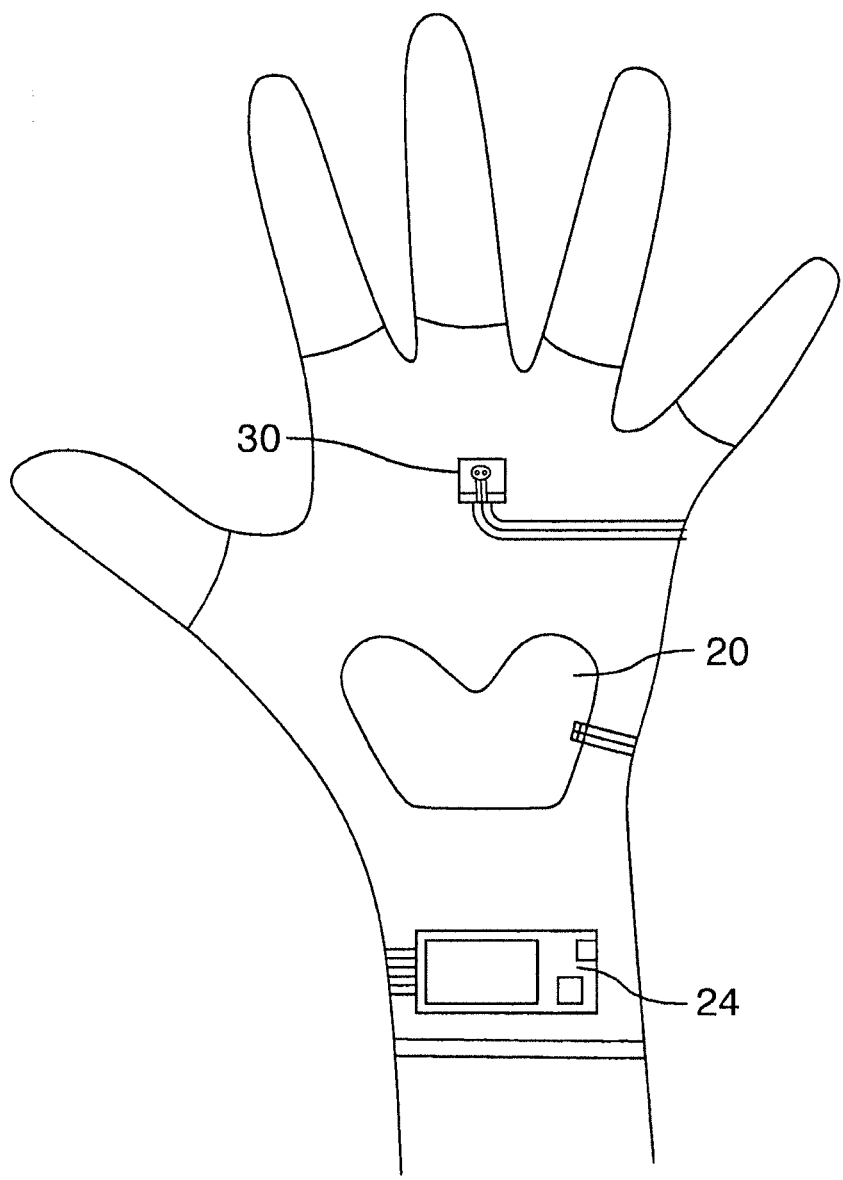
FIG. 8 is a bottom plan cutaway view showing components inside of the fingerless CPR assist glove of FIG. 5.

It will be understood that "glove" may also refer to a fingerless glove. By omitting the fingers on a glove-like wearable article, the CPR assist device may be able to fit more CPR performers and may be put on more easily. An example of a fingerless CPR assist glove is shown in FIGS. 6-8. FIGS. 6 and 7 show the fingerless CPR assist glove from a top plan view (i.e., corresponding to the back of the hand), the latter being a cutaway view showing components the inside of the glove. FIG. 8 shows components inside of the fingerless glove from a bottom plan view (i.e., corresponding to the palm of the hand). The fingerless glove may include components similar to the fingered glove discussed above. In the example shown, the fingerless CPR assist glove includes a processing unit 10 located on top of the glove below the wrist. There is also at least one sensor, which may include an accelerometer 16 on the top of the glove, a pressure sensor 20 on the bottom of the glove, and a pulse oximetry sensor 30 on the bottom of the glove. In the example shown, the pressure sensor 20 is in the form of a pressure pad over the palm area. The pulse oximetry sensor 30 is shown located in the middle of the palm, but may be located at other suitable locations. The pulse oximetery sensor 30 may be used to sense the patient's blood oxygenation level and heart rate. The pulse oximetry sensor 30 may also be used in the fingered glove discussed above. There is also at least one feedback component, which may include a visual display 28 located on a sleeve 26 on the top of the glove. There is also a power supply 24, which may be located on the bottom of the glove, below the wrist.

Figure 9:
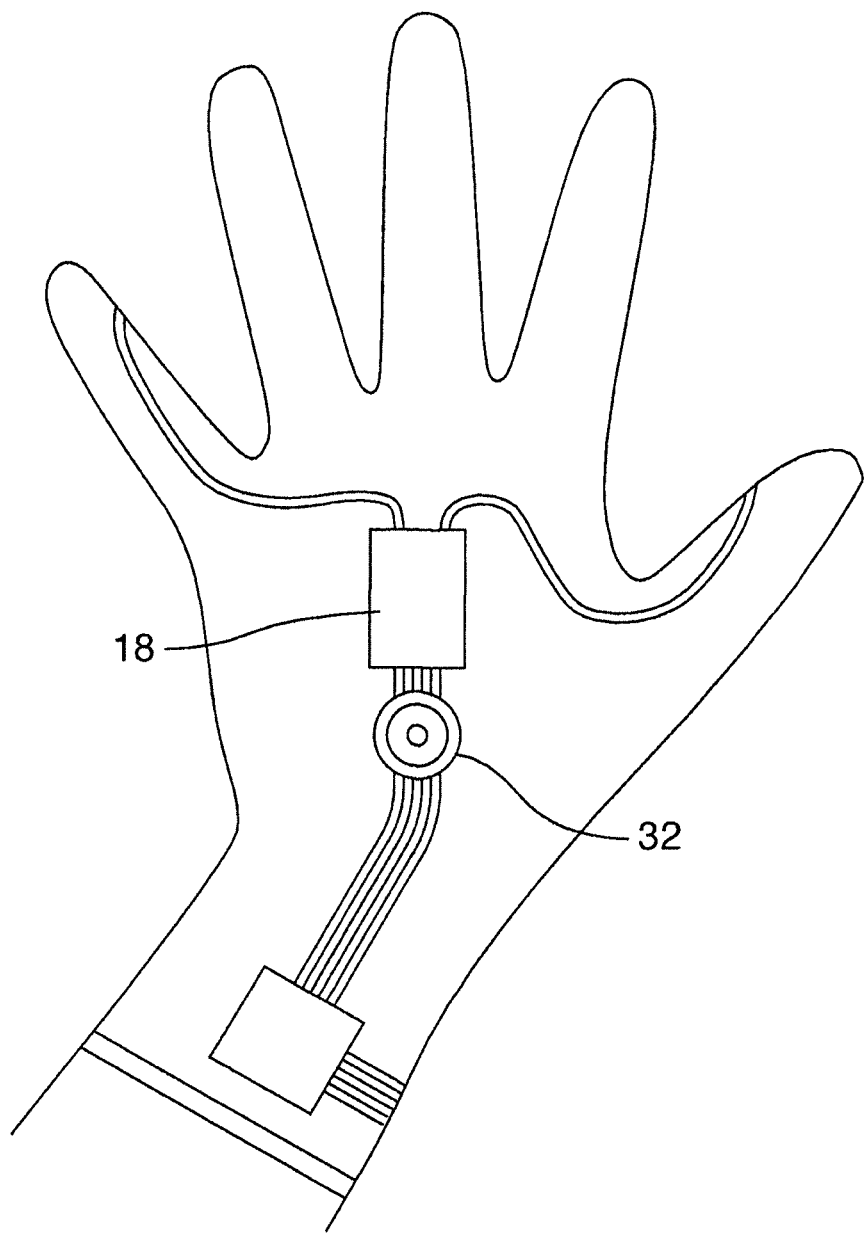
FIG. 9 is a top plan view of a simplified CPR assist glove.

In some aspects, the CPR assist device may be simplified, for example as a simple glove as shown in FIG. 9. In the example shown, there is no sleeve, and feedback to the CPR performer is conveyed by an audio feedback. A processing unit 10 and an ECG sensor 18 are also shown as an example, however other sensors and components may be present. In such a simplified device, the device may be inexpensive and may be disposable.

Figure 10:
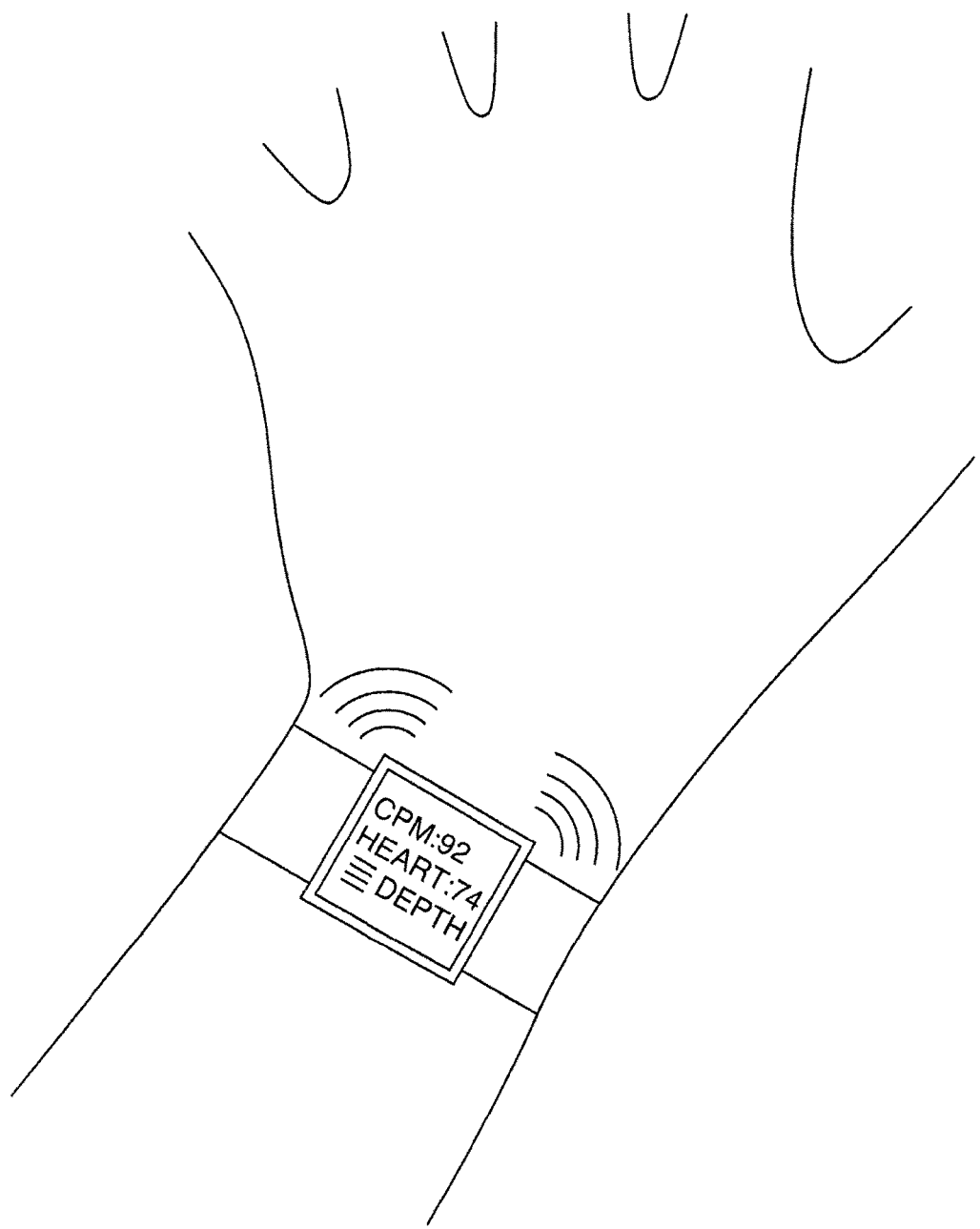
FIG. 10 is a top plan view of a wrist-wearable form of the CPR assist device.

In some aspects, there may be only one large hole for all the fingers to slide through, or the device may be in the form of a palm strap or wrist strap. An example of a wrist-wearable CPR assist device is shown in FIG. 10, which may be a wrist-strap or may be a wristwatch. The wearable article may be composed of several connected pieces, and may be made of hard or flexible plastic material instead of or in combination textiles. The wearable article may be customized and fitted for the CPR performer. It will be understood that the components discussed above may be present in these different variations, and may be positioned at different locations as suitable.

Although the wearable article has been described as a glove, it should be understood that the CPR assist device may be in the form of other wearable articles. The CPR assist device may be in the form of an intuitively wearable article (e.g., similar to a common article of clothing), where the performer can simply put on the device and perform CPR as normal, or the device can be put on the patient easily with no modifications to the CPR procedure and no external devices to worry about. By including sensors in fixed positions in the CPR assist device rather than separately or externally, the sensors may be more likely to be placed in correct positions on the patient than when using external sensors.

Sensors

The CPR assist device may include a number of different sensors for detecting patient information and parameters of the CPR being performed. Such information may include depth of compression, compression rate, compression angle, patient heart rate, hand positioning, patient body temperature, patient body type, and patient blood oxygenation level. Sensors include physiological sensors, pressure sensors, position sensors, and movement sensors. Discussed below are pressure sensors, accelerometers, and ECG sensors. Other sensors may be used in addition to or as alternatives to these sensors. Other sensors may be incorporated into the device in order to obtain additional information as desired.

Data from the sensors may be processed or analyzed and provided as feedback to the performer. The raw data or processed data may additionally or alternatively be stored in a memory in the device or in a separate computing unit, such as a base unit, for later retrieval. The raw data or processed data may additionally or alternatively be transmitted to a separate computing device.

Pressure Sensors

Pressure sensors may allow for detection of compression rate and for providing the CPR performer with feedback information based on the amount of force applied during CPR. The pressure sensors may be selected to be comfortable for the patient, since these may be directly against the patient's chest. Therefore, flexibility, durability, and thinness may be desirable properties. In some aspects, the pressure sensors may be thin, tactile, single element load sensors based on the piezoelectric effect, such as Tekscan Flexi-force™ sensors. By piezoelectric effect, it is meant that the electrical resistance of each pressure sensor varies inversely with applied pressure. Other types of pressure sensors may be used, such as a mechanical sensor or a capacitive sensor. A possible type of pressure sensor may include sensory components embedded into the wearable article itself, for example in the form of interwoven conductive and non-conductive yarns which result in capacitance changes as the yarns are compressed. Another possible type of pressure sensor may use a strain gauge, which may determine deformation during compression and translate this deformation to pressure. Yet another possible pressure sensor may use piezo resistive integrated semiconductor technology such as force sensitive resistors (FSR).

The pressure sensor may be used to detect the occurrence of CPR compressions. This may allow the CPR assist device to inform the performer of the number of compressions remaining in a cycle. By a "cycle" is meant a pre-determined number of compressions followed by a pre-determined number of breaths. One cycle may consist of 30 compressions and two breaths, though other orders and numbers of compressions and breaths may also be suitable. The specific number of compressions and breaths per cycle may be based on accepted CPR guidelines and may change as CPR guidelines are changed. The device may tell the performer how many compressions he or she has performed, or it may tell the performer how many compressions are remaining in a specific cycle. The pressure sensor may be used to calculate the compression rate. Upon completion of each cycle, compression rate information may be calculated by timing the duration of the cycle. This data may be relayed to the performer, so that he or she can adjust his or her compression speed for a subsequent cycle. The compression rate information may also be provided in real-time so that the performer can adjust speed during a cycle. The pressure sensor may also be used to collect force data. The performer may be provided with force readings from the sensor, for example at four locations on the palm. This information feedback may allow the performer to distribute force more evenly with his or her hand.

One example of the software to interpret the pressure sensor data is now described. Only one pressure sensor may be needed in determining the compression rate. The pressure sensor may generate a voltage signal proportional to the pressure sensed. The occurrence of a compression may be detected based on the signal exceeding a predetermined threshold value. The number of compressions already performed or yet to be performed for a cycle may be calculated and may be communicated to the performer. The maximum force applied during a compression may also be calculated from the sensor signal and may be communicated to the performer as an average per cycle or in real-time per compression. To calculate the compression rate, the number of compressions is divided by amount of time (e.g., in minutes) it took to complete the compressions. There may be a separate timer (e.g., in the processing unit) responsible for providing the time, or there may be a timer included with the pressure sensor. The compression rate may also be provided as feedback to the performer as an average or in real-time. Other pressure data may be calculated and provided to the performer.

Accelerometer

The accelerometer may carry out motion and position detection. One type of position detection is to detect the position of the performer's hand in relation to the patient or to a desired position for performing CPR. Information sensed by the accelerometer may be used to calculate the compression depth and compression angle. There may be separate accelerometers for measuring compression depth and compression angle, or a single accelerometer may be used to carry out both measurements. The acceleration may be used to measure addition information, which again may be done by the same single accelerometer or may be done by additional accelerometers.

In an example, the accelerometer may measure acceleration and tilt in two Cartesian axes, specifically the X (i.e., forward-backward) and the Y (i.e., left-right) directions. One example of a suitable accelerometer is the ADXL202 by Analog Devices. In another example, the accelerometer may measure acceleration and tilt in three Cartesian axes, specifically the X, Y and Z (i.e. up-down) directions. One example of a suitable accelerometer for this is the ADXL330 by Analog Devices. This component may be used to measure the angle of each compression as well as the average compression depth throughout a cycle of CPR. Alternatively, the compression angle may be measured by a separate accelerometer that may be located separate from the accelerometer for measuring compression depth. In the case of a CPR assist glove, an accelerometer for measuring compression depth may be located on the back of the hand, while a separate accelerometer for measuring compression angle may be located on the side or the top of the wrist. The separate angle sensor may be designed into the processing unit on the top side of the wrist.

The ADXL202 is based on MEMS technology. Enclosed in a 5 mm×5 mm×2 mm package, the accelerometer incorporates a polysilicon spring extended structure. Deflection of this spring structure is measured using a capacitor and the deflection is translated into an output signal. The ADXL330 may be available in a small, low profile 4 mm×4 mm×1.45 mm package on a single monolithic integrated circuit, with a signal conditioned voltage output. This accelerometer measures acceleration with a minimum full-scale range of +/−3 g. It can also measure the static acceleration of gravity in tilt-sensing applications, as well as dynamic accelerations resulting from motion, shock, or vibration. Other accelerometers may also be suitable, such as those with higher maximum acceleration measured and/or better measurement resolution.

Where compression angle is measured by a separate accelerometer, this may be done using a standard accelerometer similar to that used for measuring compression depth. In an example, the compression angle is measured by an accelerometer measuring acceleration in the X and Y axes, such as the ADXL322 by Analog Devices. Data from the compression angle measuring accelerometer may be passed through a data filter, such as a low pass filter. Trigonometric algorithms may then be used to determine the angle of the compression from the measured data. The compression angle sensor may be located in a fixed position relative to the performer's arm (e.g., on the wrist) to provide more accurate information on the angle of the performer's arm relative to the patient's body. Where the processing unit is located on the top side of the wrist, the angle sensor may be integrated into the processing unit. Using this compression angle data, feedback may be provided to the performer to help maintain the performer's arms at a desired angled (e.g., ninety degrees) relative to the patient's chest.

Measurements by the accelerometer along the Z-axis (i.e., up and down) may be used to calculate the compression depth. Measurements along the X-axis (i.e., back to front) and/or the Y-axis (i.e., left to right) may be used to calculate the angle of compressions. Feedback information to the performer about the compression angle may help the performer to perform compressions perpendicularly to the patient's chest. This may be the case when the accelerometer takes measurements along these two axes only. If the accelerometer provides measurements in different axes, the calculations may be different, and may provide additional information (e.g., compression angles in more than one plane). The measurements and calculations from different accelerometers may be adjusted as necessary in order to obtain the desired information.

In the example described above, acceleration measurements in the measurement axes may be converted into a digital format where necessary using suitable analog to digital conversion circuitry. The digital information may then be analyzed by the processing unit. This analysis may involve integrating the acceleration measurements twice to obtain displacement measurements. The data may also be filtered using standard filtering algorithms in order to obtain cleaner data.

Similarly, the compression angle may be calculated from the accelerometer measurements and an average compression angle for each cycle may be communicated to the performer. The compression angle may also be calculated for each compression and this information may be provided in real-time to the performer.

Although the discussion above was with regards to a specific accelerometer, other accelerometers may be used in the CPR assist device. Other possible accelerometers may detect movement in only one axis, in any two axes, or in all three axes of direction. Having measurements in all three axes may be useful. Measurements in the Z axis (i.e., up-down direction) may be used to determine displacement in the direction of compression, however since the accelerometer may not be perfectly level, measurements in the X and Y axes may be used to determine the inclination of the accelerometer in order to more accurately calculate the compression depth. The accelerometer may also detect angular movement in addition to or in place of movement in the Cartesian axes. Measurements from the accelerometer may be used to calculate different compression parameters and this information may be provided to the performer.

Although the accelerometer was described as providing position and movement detection, the CPR assist device may have separate position and movement sensors. Other possible position sensors include optical sensors and ultrasonic position sensors. Other possible movement sensors include tilt sensors.

ECG Sensor

The CPR assist device may include an ECG sensor to detect the heart rate of the patient and this information may be provided to the performer. The ECG sensor may include at least two electrodes through which the patient's ECG is detected. The ECG sensor may also include a ground electrode. Where two electrodes are used in a CPR assist glove, the electrodes may be placed on the tips or bases of two opposing fingers or on the palm of the hand. Only two electrodes may be required to measure non-specific ECG data, such as heart rate and QRS complex peaks, although additional electrodes may be used for recording other physiological data.

In an example, the ECG sensor may be fairly small and compact, to reduce the space it requires on the device. One example is the MSOP-8 package. The sensor may include an amplifier to amplify the signal from the electrodes, for example where the sensed physiological signal is of small amplitude. Other signal processing, such as filtering or noise reduction, may be included in the sensor. The amplifier may be a combination of an instrumentation amplifier and a dual op-amp. Other configurations for amplifying the sensor signal may be used as suitable to the application.

Filtering of the amplified signal may not be required if the desired ECG data is detectable from the signal received from the electrodes, for example, where the QRS complex of a typical ECG waveform is distinguishable and the effect of noise is negligible. Cable artifact that may contribute noise to the signal may be reduced by keeping the electrodes fixed in place on the glove, and keeping any wires attached to the electrodes short and also fixed in place.

An additional op-amp may be used to prevent baseline wandering. This may allow for the signal to maintain a constant DC level, regardless of the impedance being presented to the electrodes by the skin of the patient, which may vary over time. This additional op-amp may be used as an analog integrator to integrate the DC signal from the instrumentation amplifier, and this may be fed back to the instrumentation amplifier. This may prevent wavy traces from occurring in the ECG waveform, which may simplify programming of a heart rate detector by keeping threshold levels relatively steady.

The electrodes may be standard electrodes, which may be gel-based or dry, clip-ons, reusable or disposable, or other common electrode types. In the case of dry electrodes, a conductive metallic strip positioned in the fingers of the glove may serve as the sensor area. In the case of disposable gel clip-on electrodes, the electrodes may be clipped onto the fingers of the glove and the adhesive pulled back to expose the gel. This configuration may be suitable when the patient's chest is exposed. The adhesive electrodes may adhere to the patient's chest, marking the correct hand position for CPR so that this correct position only has to be found once. The correct hand position for CPR may be instructed by the CPR assist device, for example via a visual or audio feedback. The connection between the electrodes and the fingers on the glove may be a simple conductive link established by simply pressing the fingers down against the electrodes.

An example of the software to interpret the ECG sensor data is now described. The heart rate may be calculated from the ECG signal using a simple algorithm. An ECG reading is taken for a pre-determined length of time, such as six seconds, and the number of heart beats that occur during that time are counted. The performer may be instructed by the device not to move the electrodes until the pre-determined length of time has passed. The performer may be provided with feedback (e.g., a visual or audio countdown) as to how much longer the electrodes have to be in place. The number of beats during that length of time is multiplied by a suitable factor to calculate the number of heart beats per minute (e.g., where the length of time is six seconds, the number of heart beats detected would be multiplied by ten). The calculated heart rate may be communicated to the performer, for example through a visual display. A heart beat may be detected using threshold values to detect the presence of a QRS complex.

In an example, analog data from the ECG sensor may be continuously fed in to the processing unit at a fixed rated, for example at 16 Khz. Occurrences of the QRS complex in such a signal may be detected whenever the signal crosses a certain threshold value. Implementations of QRS detection software would be known by persons skilled in the art.

In some aspects, to eliminate transient data from being collected by the processing unit, the performer may be given a few moments to place the electrodes on the patient. This may simplify the software for recognizing when the electrodes have been placed and a proper ECG signal is being received. In some aspects, the device may be able to recognize proper placement of the electrodes or a proper ECG signal, so that a fixed time delay to allow for placing of the electrodes may be not necessary.

Other Sensors

Other sensors may be included in the CPR assist device. One possible sensor is an ultrasonic sensor, which may be useable as a position sensor. This sensor may emit a high frequency ultrasonic pulse with an attenuation and reflection time that can be measured. The ultrasonic reflectance changes as the density of tissue changes from soft tissue to bone. Using this data, the correct position of the performer's hands can be determined, and the performer may be instructed or guided to accurately position his or her hands over the patient's sternum.

Another type of sensor may be a separate sensor for compression angle. As described previously with regards to the accelerometer, a compression angle sensor may be implemented using an accelerometer. Another possible implementation of a compression angle sensor is using a tilt sensor. A tilt sensor may include a simple switch that activates when an arm on the sensor is lifted to a certain angle, or when a sliding mechanism slides down when lifted to a certain angle and completes an electrical connection. In the case of the CPR assist glove, such a sensor may be embedded in the wrist portion to monitor the angle of compression. Compression angle may be one element to be considered in performing proper CPR. Currently established CPR guidelines direct the CPR performer's hands to be locked together and the arms to be perpendicular to the victim's chest. The proper compression angle may help to achieve maximum transfer of force. The proper compression angle may also reduce strain and exhaustion for the CPR performer.

Yet another type of sensor may be a body type sensor. By body type is meant the size, fat-to-muscle ratio, body mass index, or any other common measurement of body shape or size known in the art. The body type sensor may use ultrasonic or impedance sensors to determine the patient's body type. An ultrasonic sensor may determine the chest depth of the patent by determining the distance from the sensor on the CPR assist device to the ground below the patient. An impedance sensor may determine the body fat ratio of a patient by measuring the patient's body impedance between two electrodes. Other methods and sensors for determining body type may also be used. Alternatively or in addition, the CPR assist device may allow the performer to manually select the patient's body type. By having information on the patient's body type, the CPR assist device may provide more suitable CPR instructions to the performer (e.g., deeper compression depth for a large patient or shallower compression depth for a smaller patient). Thus, the CPR assist device may be adaptable for any body size from infant to large adult.

Other physiological sensors are possible, including oximetry sensors which measure oxygen levels in the patient's blood, and body temperature sensors. As an example, an oximetry sensor may measure oxygenation of the patient's blood by transmitting light of two different wavelengths (e.g., red and infrared) through the patient's skin. Light reflected from the patient may be detected by the sensor, and oxygenation of the blood may be determined based on the relative reflectance and absorbance of the two wavelengths. Information on the oxygenation of the patient's blood may be analyzed to determine whether the patient requires artificial respiration, and the CPR assist device may provide feedback to the CPR performer accordingly. The oximetry sensor may also be used to determine the patient's heart rate instead of using the ECG sensor, based on sensing the pulsatile component of blood flow in the patient.

The CPR assist device may also have a sensor to allow the device to turn on automatically when a CPR performer wears the device. This may be a capacitive sensor connected to the on-switch that is able to determine whether the device is being worn. This may simplify use of the device by forgoing the need to activate the device, and may speed up the CPR process. An example of a capacitive sensor suitable for this application is the QProx QT100Tivi one-touch sensor. The sensor is capable of sensing the change in capacitance from a nearby electrode. In the case of a CPR assist glove, this sensor may be implemented by embedding an electrode material (e.g., thin and flexible indium tin oxide) into the inside of the glove. When the CPR performer's hand is inserted into the glove, the hand changes the capacitance from the electrode, which is sensed by the capacitive sensor. The capacitive sensor may be able to detect changes through materials, for example if the performer is wearing a latex glove. The turn-on feature of the capacitive sensor may be fail-safe, which is if the capacitive sensor deactivates in error, the CPR assist device may not automatically turn off, and a manual deactivation may be required after the device is activated. Other methods and sensors for triggering automatic activation of the device may be used.

The sensors have been described as collecting relevant CPR data. However, the sensors may also be used to detect the occurrence of an event. By "event" is meant a specific step or stage in the CPR procedure. For example, the device may detect when the CPR performer is ready to initiate chest compressions by using a compression angle sensor to determine when the performer's arms or hands are at the correct angle (e.g., perpendicular to the patient's chest), or the device may detect when the performer's hands are on the patient's chest using pressure sensors. Different feedback for each step in CPR may be provided to the performer based on the detection of such events.

Processing Unit

The processing unit may contain the instructions for data acquisition and analysis of a sensed parameter. Furthermore, the processing unit may send out instructions and/or data to the other components, such as the sensors and the feedback component.

The processing unit may be able to handle analog data, which may be desirable in cases where some sensor data are analog. In some aspects, the processing unit may have available analog to digital converting inputs. The processing unit may also have the ability to time the duration of certain events. When calculating pulse width, such as in the case of the accelerometer, or heart rate, such as in the case of the ECG sensor, a timer in the processing unit may be used in the data acquisition process. The computations being performed on incoming data are typically not mathematically rigorous, and consequently, an 8-bit microcontroller with floating point arithmetic may be sufficient for use as the processing unit. Where data may be transmitted or received, the processing unit may be capable of transmitting and receiving data. Such transmission and reception may be wired or may be carried out wirelessly, and the processing unit may be selected to enable such functions. The processing unit may allow the direct transmission of asynchronous data from the transmitting board to a host receiving station or other separate computing device. In some aspects, the processing unit may send and receive data to a separate transmission/reception module that coordinates this communication.

In an example, the processing unit may be a microcontroller such as the ATMEGA32 AVR 8 bit RISC processor, the ATMEGA128 processor from Atmel, or the MSP430 series microcontrollers from Texas Instruments. In these example processing units, the integration of timers and analog to digital converters on the controller may allow for data collection and analysis with few external components. Analog signals may be connected directly to port pins and digital signals may be timed with any of the three onboard timers.

The processing unit may also have a long-term memory component. This memory may be used for storage of CPR parameters for later download and analysis. In this way, the processing unit may be used as a "blackbox" for recording medical and CPR data during resuscitation or training. In the example processing units described above, the microcontrollers may include SRAM and/or EEPROM useable for this purpose. The memory component may also be separate from the processing unit, for example as a removable Flash memory. The memory may also be external, for example as a removable memory card or a micro SD card. Having a removable memory may make it easier for data gathered during a CPR session to be downloaded for analysis.

In some aspects, the processing unit may enable the user to download updated software and various simulation models into the CPR assist device. This may allow the device to be adaptable to performing CPR in different situations or on different types of patients. The processing unit may have a data port to enable wired downloading, or downloading may be done wirelessly.

In some aspects, the processing unit may be programmable by connecting the device to a separate computing device. In some aspects, the processing unit may only be programmable by the manufacturer, so that average performers cannot accidentally change the operation of the CPR assist device.

Power Source

The CPR assist device may be adapted to be connected to a power source. The CPR assist device may include its own power source contained in the wearable article, which may increase the ease of use of the device. This power source may be in the form of a battery or a rechargeable cell. In other embodiments, the CPR assist device may include a power source connector that is to be connected to an external power source, such as a wall socket or an external battery. This may be suitable where the CPR assist device is part of a larger emergency kit. The CPR device may also be adapted to be connected to a power supply in a base unit, which in turn may be connected to an external power source.

In some aspects where the CPR assist device is powered by rechargeable batteries, the device may be plugged directly into a wall, a computer, a car jack, or a similar power source to be charged. The device may have low power consumption and the batteries may be designed to last long periods of time. In some aspects, if battery level is low, an audible and/or visual (e.g., a light) signal may be emitted to warn the performer.

Using a smaller battery may enhance wearability or ease of use of the CPR assist device. In an example, a one-cell lithium polymer battery may be used, which provides small battery size and high energy density. A DC/DC converter boost may be used to increase the nominal voltage of the battery to a desired operating voltage for the device. Other possible power supplies may be adapted to the device, as would be known to a person skilled in the art.

Feedback Component

Figure 11:
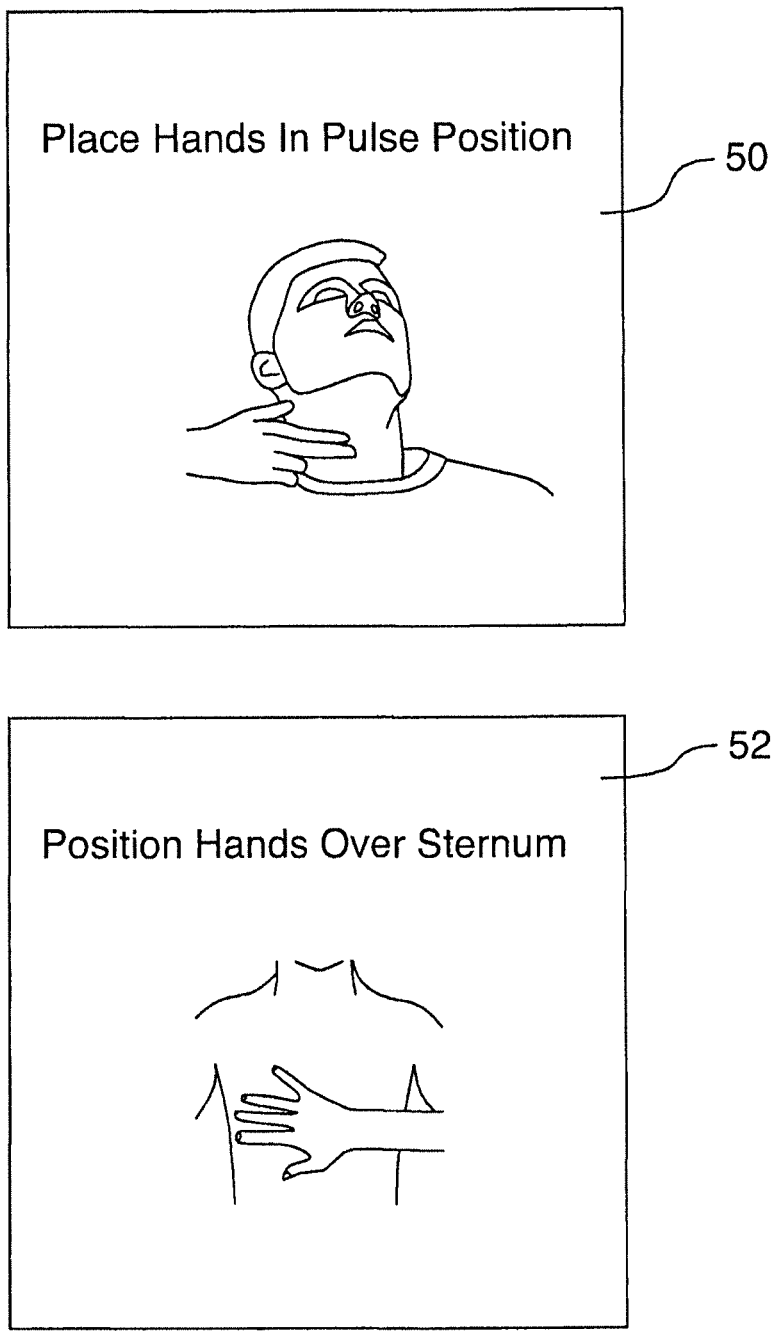
FIG. 11 shows example visual feedback provided by the CPR assist device.

The feedback component may provide the performer with raw data from the sensors or processed data from the processing unit. This feedback may be provided to the performer in a variety of ways, such as visual, audio or tactile. In some aspects, the feedback component of the CPR assist device may provide the performer with visual feedback. FIG. 11 shows two examples of visual feedback that may be provided to the performer. In screen 50, the performer may be instructed to place his or her hand in position to check for a patient's pulse, to determine if CPR is necessary. In screen 52, the performer may be instructed to position his or her hands over the patient's sternum at the start of the CPR procedure.

Feedback data may be displayed on a screen, such as an LCD screen directly embedded into the CPR assist device. There may be more than one feedback component on the device (e.g., two screens or a screen and an audio tone), which may provide different feedback information to the CPR performer, or may allow the performer to receive the same information in different forms. The feedback component may be provided in a separate base unit to be used with the device. In some aspects, the data is transmitted to a separate computing device, such as a personal computer or a portable wireless device for display. This transmission may be done wirelessly or may be wired.

In an example, a 40×2 character LCD display may be used to display output information. The specific model for this example may be TM402CDAU6. The display may be tethered to the CPR assist device rather than being embedded in the device. This may be desirable, for example, where the device is in the form of a glove and the display is a large LCD screen that would not fit comfortably on the glove.

A graphical LCD with color support may be used in some aspects. A graphical LCD may allow for display of pictures, which may provide visual CPR instructions. Also, such an LCD may be able to display the ECG signal in its entirety, rather than text-based information. The LCD display may be capable of providing color displays and/or text displays. Other suitable display devices would be known to a person skilled in the art.

In some aspects, feedback may be provided using a separate computing device, such as a laptop, a personal computer, portable device, or a base unit. A computer may provide a larger viewing screen, ample processing power and storage and may aid in data analysis and transmission. A computer software package may be used on the computer to interact with the CPR assist device. Such a software package may be used for independent training of a single CPR performer, or for training a group of performers. The software package may be capable of receiving and/or analyzing data from multiple CPR assist devices at one time.

In some aspects, an audible feedback may be provided. This feedback may be in the form of voice commands so that the performer does not have to read the display. The audio feedback may include a piezo element that emits a sound every time a compression should be performed. This sound may enable the performer to maintain an efficient and accurate rhythm. Methods of providing rhythmic feedback may include any means of generating a tone, for example a tone generator, a buzzer, or a piezo element.

The audio feedback may also be in the form of audio instructions which may be in addition to or in place of visual instructions to the performer. Audible cues such as "Compress Faster" or "Compress Deeper" may be provided in real-time to guide the performer through the CPR procedure. Such audio feedback may be conveyed via a speaker (e.g., a magnetic speaker or a piezo speaker) and possibly an amplifier on the CPR assist device. The speaker and/or amplifier may be thin so that it is not cumbersome, which may be desirable where these components are provided on the device. Specific audio cues may be stored in the processing unit in the form of audio files.

Other types of feedback may be implemented, such as tactile feedback (e.g., a small vibration), which may be used to control the rate of compression. The CPR assist device may also have a combination of different feedback types to provide a wider range of information to the performer. Other types of feedback may be given to the user (e.g., if the compression depth is to shallow or deep, or if too much or too little force is being used), and this feedback may be visual, audio, or tactile. The type of feedback may be different depending on the information being conveyed, and the feedback type may be selectable by the performer.

Wireless Transmission

In some aspects, the CPR assist device may be capable of transmitting data wirelessly. The CPR assist device may also be capable of receiving data or instructions wirelessly from a separate computing device.

In some aspects, a separate computing device is used, which may be a separate base unit dedicated to the CPR assist device. The separate computing device may receive data from the CPR assist device, and may contain a visual display, such as a graphic LCD, that may be used to display instructions and data relevant to CPR. To facilitate the link between the transmitting and receiving ends, a wireless link may be established, or the transmission and reception may be done by wired means.

In an example, the transmitter/receiver set being used may be the TX-433 series from Linx Technologies. These transmitters can transmit over a long distance (e.g., up to 3000 feet) and at reasonably high speeds (e.g., 10 kbps). No external components may be required for this transmitter and receiver, which may further decrease board size. The transmitter may be connected to an antenna, such as a ¼ whip antenna or a low profile ceramic antenna, to further enhance the quality of the wireless link. The antenna may be kept small so as to minimize the overall size of the system. The transmitter may be connected directly to the processing unit so that asynchronous serial data can be fed directly into the transmitter module.

A protocol for transmission of data from the device may be a standard wireless RF protocol. The Bluetooth protocol or other suitable short-range wireless protocol may be suitable for transmission of data. The Bluetooth protocol may be desirable since it would allow communication between the CPR assist device and other wireless devices using this protocol, such as cellular telephones, personal digital assistants, data phones, or similar devices.

In some aspects, most of the data analysis may occur at a separate computing device such as a dedicated base unit. This may minimize the number of components (and hence board size) on the CPR assist device. The separate computing device may contain a processing unit for carrying out data analysis, and may also have a speaker module for voice commands, a visual display for display of data and instructions, and an external memory (e.g., an SD card or a Compact Flash card) for data storage and retrieval. This memory may be used to log the events of a CPR training session, test, or real life medical emergency. The data may also be sent directly from the CPR assist device to a separate computing device. This data may later be downloaded and analyzed to assess the performer's technique during the CPR event. Software may be available for personal computing systems so that the CPR assist device may be run on a standard home computer instead of a specialized base unit.

Software Algorithm

The CPR assist device implements a software algorithm in the processing unit to assist the performer in performing CPR. This algorithm guides the performer in performing CPR, and may be based on medically established guidelines for performing CPR. An example of an established guideline for performing CPR is as follows:

1. Call 911
2. Check the victim for unresponsiveness. If there is no response, Call 911 and return to the victim. In most locations the emergency dispatcher can assist the CPR performer with CPR instructions
3. Administer Breaths
4. Tilt the head back and listen for breathing. If not breathing normally, the performer should pinch nose and cover the mouth with his or her own and blow until the patient's chest rises. Give 2 breaths. Each breath should take 1 second
5. Chest Compressions
6. If the victim is still not breathing normally, coughing or moving, begin chest compressions. Push down on the chest 4 to 5 cm 30 times right between the nipples. Pump at the rate of 100 pumps per minute, faster than once per second.

In an example, the software algorithm instructs the performer to carry out a CPR procedure as follows:

1. Attempt to get the patient's pulse and instruct performer to check if the patient is breathing.
2. If the patient's heart rate is detected and/or the patient is breathing, instruct the performer that CPR is not required.
3. If the patient's heart rate is not detected and the patient is not breathing, instruct the performer to begin compressions.
4. As compressions occur, compression force and compression depth data is gathered via the respective sensors on the CPR assist device. Force data may be displayed as visual feedback to the performer as compressions are given.
5. After administering a pre-determined number of compressions, the average compression depth may be displayed. The performer may be instructed to give two breaths and check the patient's pulse via a ECG sensor.
6. If the patient's heart rate is detected, return to step 2, otherwise return to step 3.

The CPR assist device may communicate with a separate computing device that may also carry out analysis of a sensed parameter, or may store data from the device for later retrieval and/or analysis.

The CPR assist device may be adaptable to specific emergency scenarios. Software related to specific emergencies may be easily downloaded into the device. Such download may be done by a wired connection or wirelessly. Provision and downloading of new software may be limited to certain authorities, to prevent tampering. Depending on the specific situation, the device may instruct the performer on the proper protocol for that event. For example, the instruction set in the case of a drowning may be different then the instruction set in the case of a heart attack or the protocol for an infant may differ from that for an adult.

Furthermore, in training mode, various simulations may be run while using the CPR assist device. These simulations may provide CPR training for a multitude of unique situations. In some embodiments, the device may include a link to a computing device in which a simulation can be run. The device may transmit to the computing device over a wireless link, such as via radiofrequency (RF), Bluetooth or any other means of communication without wires. Such training may take place over a communication network, such as the Internet, to allow for online independent learning.

Simulations may be real life scenarios with real life variables and the device may measure whether the individual being trained is responding correctly. These simulations may be software based and graphically oriented. As CPR guidelines are updated, the CPR assist device may also be updated to reflect changes. A programming interface may be provided in the device to enable download and installation of new guidelines, simulations, and/or instructions. Such downloading may take place over a communication network, such as the Internet.

Base Unit

Figure 12:
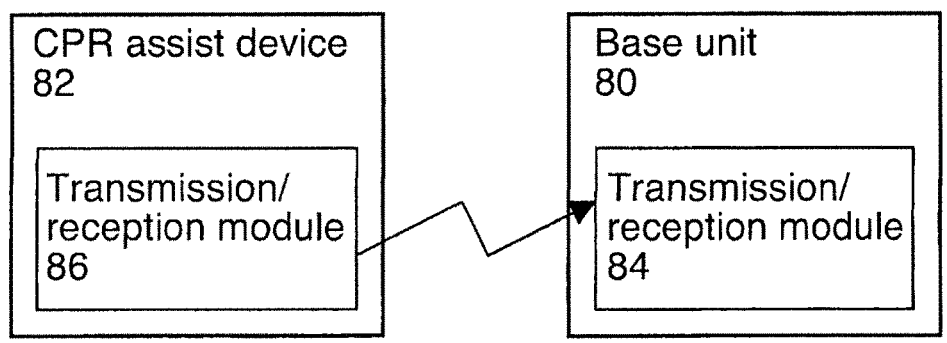
FIG. 12 is a schematic view of a system including the CPR assist device and a base unit.

In some aspects, the CPR assist device may be provided as part of a system, which includes the CPR assist device and a base unit. The base unit may be in the form of a container for the CPR assist device. In some aspects, the base unit may be suitable for defibrillation, such as a defibrillator. As shown in FIG. 12, the base unit 80 may communicate with the device 82 wirelessly, and this communication may be facilitated by transmission/receiver modules 84,86 as shown or by antennae (not shown) included on the base unit and/or the device. Such transmission/receiver modules or antennae may also allow the system to establish a communication link with medical authorities. For example, the base unit may be capable of establishing a landline communication link with 911. In another example, the base unit may be capable of establishing a wireless cellular link with 911. The communication as described above may also be by wired means.

The system may also be equipped with a positioning system such as a Global Positioning System (GPS) so the location of a CPR emergency may be communicated to a medical authority. This communication may take place automatically when the system is activated for perfoiming CPR. In the case where the base unit is not intended to be moved, the location of the system may be fixed and this fixed location may be communicated to a medical authority. The location may also be communicated verbally by the CPR performer, for example through a microphone provided on the device or the base unit.

In some aspects, the feedback component may be provided on the base unit in addition to or alternative to being on the device. This may be in the form of an audio speaker on the base unit or a larger visual display on the base unit. Where the base unit is a container, the feedback component may be a visual display on the cover. The container may also include a processing unit in addition to or as an alternative to the processing unit on the device. The processing unit provided on the container may be larger and provide greater processor power than the processing unit on the device. The base unit may also provide a power source for the device. The feedback component and/or the processing unit in the base unit may perform the same tasks as discussed above in relation to the same components being provided on the CPR assist device. By providing some or all of the feedback components on the base unit instead of on the CPR assist device, the battery life of the power supply on the device may be extended.

The base unit may be useable for defibrillation. For example, the base unit may include defibrillator pads or be part of a defibrillator. In this case, the instructions and feedback provided by the system may include instructions for the CPR performer to also perform defibrillation on the patient.

The base unit may be fixed in location or may be mobile. Where the base unit is fixed in location, the CPR assist device is mobile and removable from the base unit, and the device may be free of connections to the base unit, to increase the ease of use of the device. Where the base unit is mobile, it may be mounted or connected to an external power source when not in use, for charging a rechargeable power supply in the system. The base unit may be easily portable so it can be brought to the patient's location.

Where the base unit is in the form of a container, it may be used as a first aid kit container. In addition to the CPR assist device, the base unit may container other first aid supplies, such as bandages and antiseptic.

Applications

The CPR assist device and/or the system may be used in at least the following scenarios: in simulation-based training of individuals, in maintaining CPR quality through testing, and in real life emergencies. These uses will be described in greater detail below.

In one example where the CPR assist device is used for training, the CPR assist device may be worn by the person performing the CPR or may be placed on a training device, such as a CPR mannequin. Once the CPR assist device is properly placed, the performer may proceed to perform CPR unhindered. The CPR assist device may guide the performer on the proper technique and timing of the phases of the CPR routine, for example through a display on the CPR assist device, a separate computing device, the base unit, or through other feedback means (e.g., audio feedback). In addition to the instructions being conveyed to the performer, there may also be provided additional data such as how fast the performer is performing the compressions, how deep each compression is, what angle each compression is at, what the heart rate of the patient is, and how much force is being applied during compression. The information and the type of feedback presented to the performer may be selected by the performer, and may depend on the sensors incorporated into the CPR assist device. After a training session, the data may be downloaded from the CPR assist device to a separate computing device or database, to a memory on the base unit, or stored on a memory in the CPR assist device for further analysis. The CPR assist device may allow individuals to train themselves or be trained with minimal supervision.

The CPR assist device and/or system may be used for online training as well. A separate computing device or the base unit may communicate with the device in order to receive quantitative data in real-time to assess a performer's CPR proficiency. The device or the base unit may communicate wirelessly (e.g., using Bluetooth) or through a wired connection (e.g., a USB port) with an external computing device, which may be connected to a communication network, such as the Internet. Medical personnel or other suitable authorities may then access the data online, or an online service may be used to assess a performer's abilities in CPR and certify him or her accordingly.

In the case of testing, an individual may wear the CPR assist device or put the device on a mannequin and perform a round of CPR. After completion of a test, the data may be analyzed to determine if the CPR was corrected performed. This analysis may be performed by a suitable authority, or by the device or base unit. In this way, the CPR assist device may provide an objective, standardized measure of CPR quality. Such testing may take place over a communication network, such as the Internet. In this case, data from the CPR assist device may be provided over the communication network to a suitable authority for analysis, such as a suitable testing service.

In the case of real emergencies, the CPR assist device may be worn by a CPR performer during administration of CPR or may be put on the patient. The device may guide an individual through each phase of CPR. Furthermore, data feedback may be provided to the performer in real-time so that CPR may be performed effectively and efficiently. The device may be fairly small and portable, so as to be easily stored in first aid kits, pool houses, homes, community centers, restaurants, malls or any other location where it may be needed. In the case where the CPR assist device is in the form of a glove, it may be no larger than a standard glove and may be taken on trips, hikes, or carried in a purse or backpack.

The CPR assist device, when in the form of a wearable glove, may be useful in conjunction with a defibrillator, and the defibrillator may be the base unit to be used with the device. It may provide insulation between the performer and the patient, hence speeding up the time for defibrillation by allowing measurement of the patient's heart rhythm without interference while CPR is being performed. CPR may increase the effectiveness of defibrillation.

Figure 13:
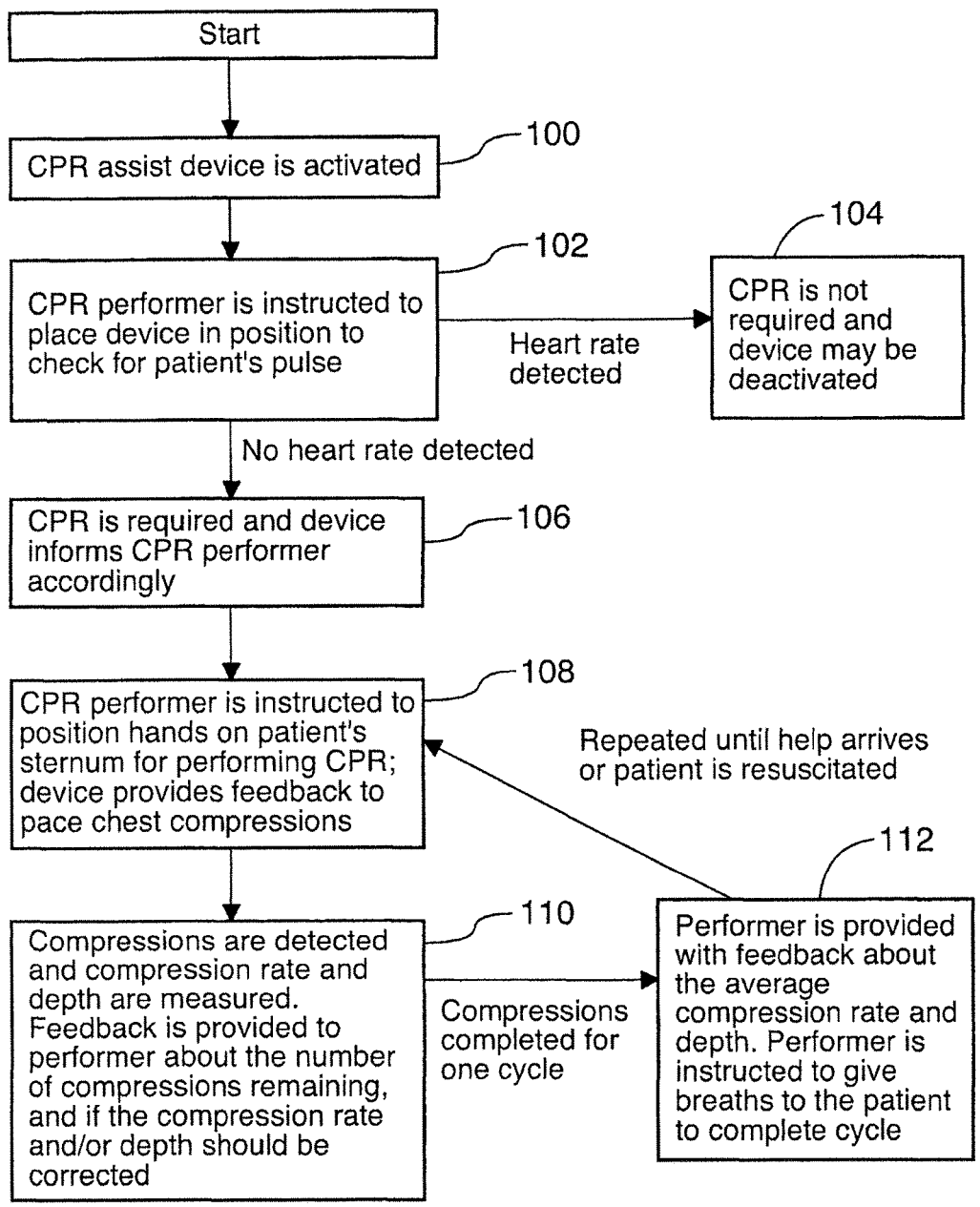
FIG. 13 is a flowchart illustrating a use of the CPR assist device for assisting a CPR performer.

FIG. 13 illustrates an example of how the CPR assist device may be used to aid a CPR performer during a CPR procedure.

At a step 100, the CPR assist device is activated. This may be an automatic activation triggered by the device being worn, either by the CPR performer or by the patient. The software may automatically run and initiate the instructions for performing CPR.

At a step 102, the CPR performer is instructed to position the device for checking the patient's pulse. This instruction may be conveyed to the CPR performer through the at least one feedback component, for example a visual feedback and/or an audio feedback. The device then senses whether there is a heart rate.

At a step 104, a heart rate is present, so CPR is not required. This may be conveyed to the performer, and the CPR assist device may be deactivated.

At a step 106, a heart rate is not detected. This may be conveyed to the performer, and the performer may be instructed to carry out CPR on the patient.

At a step 108, the performer is instructed to place hands over the patient's sternum in preparation for performing CPR. The device may provide visual and/or audio feedback to aid the performer to provide chest compressions at a desired rate. For example, the device may produce audio beeps at 100 Hz.

At a step 110, the device detects each chest compression, for example via a pressure sensor. The device may instruct the performer to perform a predetermined number of compressions in a cycle (e.g., 30 compressions). The number of compressions is recorded, and the rate and depth of each compression is also measured and recorded. The device may provide the performer with visual and/or audio feedback about the compressions, for example there may be a visual display of how many compressions remain in a cycle. There may also be feedback, for example an audio cue, if the compressions are too slow or fast, or too deep or shallow. There may additionally be an audio cue when there is a certain number of compressions remaining to in the cycle.

After the predetermined number of compressions have been completed in a cycle, at a step 112 the performer is provided with feedback about the average compression depth and rate for the cycle. This may be through a visual display. The performer is then instructed to give a predetermined number of breaths (e.g., two breaths) to the patient to complete the cycle.

After the completion of breaths, the process returns to step 108 and the performer is instructed to repeat the cycle. This continues until help arrives (e.g., medical authorities or an ambulance) or until the patient is resuscitated.

Figure 14:
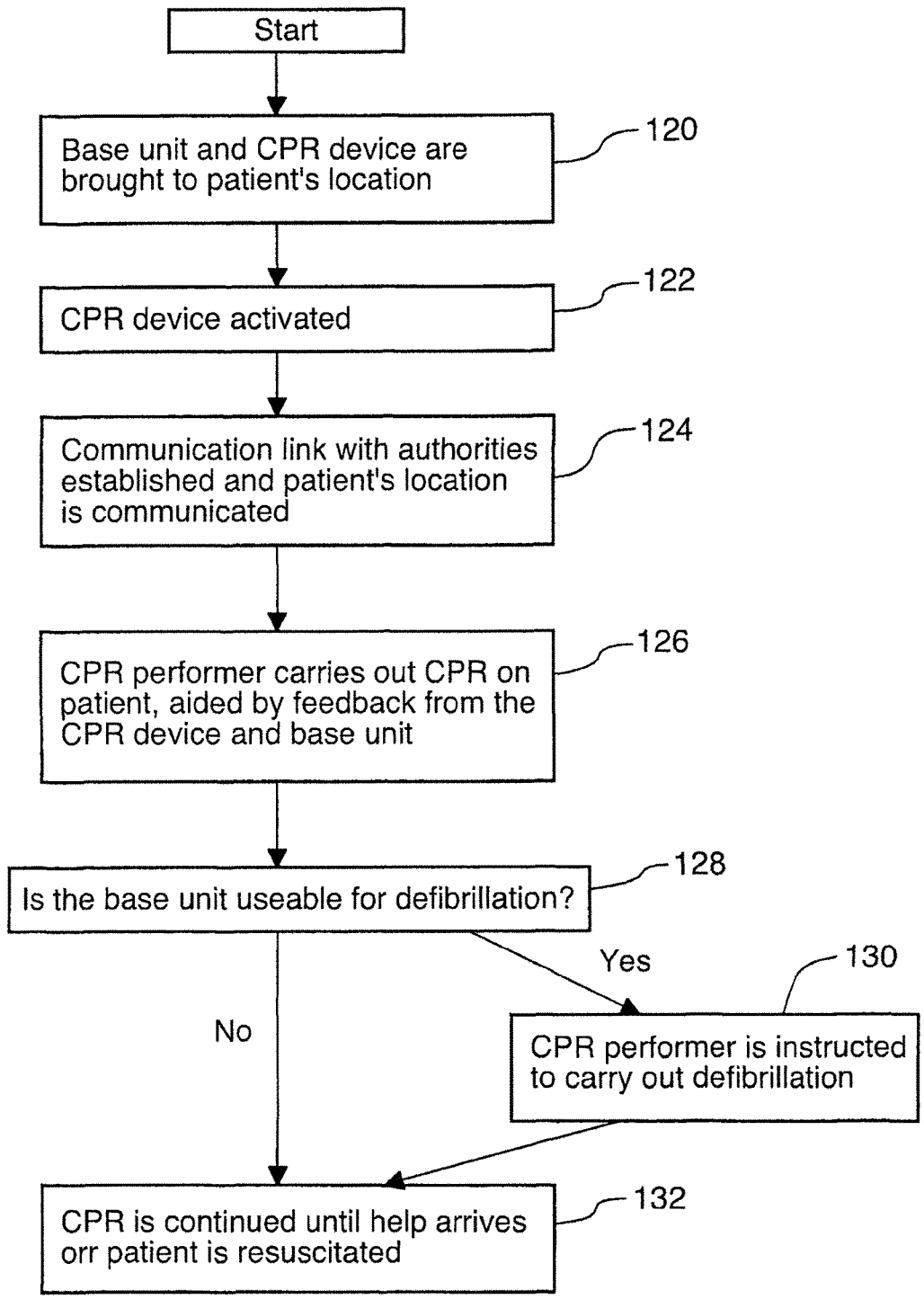
FIG. 14 is a flowchart illustrating a use of the CPR assist device with the base unit.

FIG. 14 illustrates an example of how a CPR assist system having a CPR assist device and a base unit may be used to aid a CPR performer in performing CPR.

At a step 120, the CPR assist device and the base unit is brought to the patient's location. The CPR assist device may be contained in the base unit, for example where the CPR assist device is in the form of a glove and the base unit is a container for the glove.

At a step 122, the CPR assist device is activated. This may be triggered by the device being worn by the performer or the patient. This may also be triggered by removing the device from the base unit. Activation of the device may automatically initiate the software to being instructions for performing CPR.

At a step 124, a communication link is established with the authorities (e.g., to 911). This may be automatically triggered when the device is activated. The patient's location may be automatically communicated to the authorities. This may be communicated automatically by the system (e.g., where the device or base unit is equipped with a locating system such as GPS) or the CPR performer may be prompted to communication the location verbally via a microphone on the device or base unit.

At a step 126, the performer is guided to perform CPR, as described above with reference to FIG. 13. The performer may be provided with feedback in the form of instructions or corrections where the CPR procedure is incorrect. Such feedback may be provided through the device and/or the base unit.

At a step 128, the base unit may be useable for defibrillation, for example where it is equipped with defibrillation pads.

If the base unit is useable for defibrillation, then at a step 130, the CPR performer is instructed to defibrillate the patient. The performer may be provided with instructions for placing defibrillation pads on the patient and may be guided through how to perform defibrillation. After defibrillation, the process continues to a step 132.

If the base unit is not useable for defibrillation, the process continues directly to step 132. At step 132, the performer is instructed to continue carrying out CPR on the patient until help arrives or until the patient is resuscitated.

As discussed above, the CPR assist device may be adaptable to different patients and different situations. The sensors have been discussed as being in certain positions on the CPR assist device, but these positions may be modified as necessary to obtain the desired sensing function. The positions of the sensors may be modified by the CPR performer so as to suit the specific application, or the sensors may be interchangeable. The analysis and feedback program in the processing unit may be updated as necessary. For example, it may be that compressions are more effective when performed on the patient's abdomen rather than the chest. The CPR assist device may be updated to provide this information to the CPR performer.

The CPR assist device and system is in no way limited to the specific embodiments described. Any device for the training of individuals in CPR, testing of individuals in their ability to perform CPR or for use in emergencies and that is to be wearable by the performer or the patient is covered by this application. The scope of this application is not to be limited by the listing of specific components. Any electrical or computing components may be used to satisfy the goal of the invention.

What is claimed is:

1. A wearable medical device, comprising:
a wearable article configured to be selectively attached around a torso of a patient;
one or more sensors housed in the wearable article and configured to be in physical contact with the patient when the wearable article is attached around the torso of the patient and a performer is administering cardiopulmonary resuscitation to the patient, the one or more sensors including at least one accelerometer that is configured to sense multiple of a position, an angle, or a movement of at least two of a chest of the patient, an arm of the performer, and a hand of the performer while the cardiopulmonary resuscitation is being administered to the patient, the one or more sensors configured to generate sensed data that is based at least in part on the multiple of the position, the angle, or the movement of the at least two of the chest of the patient, the arm of the performer, and the hand of the performer;
a processing unit configured to receive the sensed data from the one or more sensors and to generate movement data based at least in part on the received, sensed data; and
at least one movement component configured to receive the movement data and convey the movement data to an output.

2. The device of claim 1, wherein the wearable article includes one of a vest and a belt.

3. The device of claim 1, wherein the processing unit is positioned on the wearable article.

4. The device of claim 1, wherein the processing unit is positioned remotely from the wearable article.

5. The device of claim 1, further comprising a feedback component configured to receive the sensed data from the one or more sensors and to convey the sensed data to the output.

6. The device of claim 1, further comprising a feedback component positioned on the wearable article.

7. The device of claim 1, wherein the output includes one or more of a visual output, an audio output, and a tactile output.

8. The device of claim 1, wherein the output includes a display that is configured to display the feedback data.

9. The device of claim 8, wherein the display includes a screen.

10. The device of claim 1, wherein the feedback data includes an instruction to the performer.

11. The device of claim 1, wherein the processing unit is configured to analyze the sensed data and compare the sensed data to at least one desired parameter in a desired cardiopulmonary resuscitation procedure, the processing unit is further configured to include the comparison of the sensed data to the at least one desired parameter in the desired cardiopulmonary resuscitation procedure in the generated feedback data.

12. The device of claim 1, wherein the device is configured to automatically activate when the device is attached around the torso of the patient.

13. The device of claim 1, further comprising a memory that is configured to store the sensed data.

14. A medical system, comprising:
a wearable article configured to be selectively attached around a torso of a patient;
one or more sensors housed in the wearable article and configured to be in physical contact with the patient when the wearable article is attached around the torso of the patient and a performer is administering cardiopulmonary resuscitation to the patient, the one or more sensors including at least one accelerometer that is configured to sense multiple of a position, an angle, or a movement of at least two of a chest of the patient, an arm of the performer, and a hand of the performer while the cardiopulmonary resuscitation is being administered to the patient, the one or more sensors configured to generate sensed data that is based at least in part on the multiple of the position, the angle, or the movement of the at least two of the chest of the patient, the arm of the performer, and the hand of the performer;

a processing unit configured to receive the sensed data from the one or more sensors and to generate movement data based at least in part on the received, sensed data;

at least one feedback component configured to receive the movement data and convey the movement data to an output; and a base unit configured to be in communication with the one or more sensors, the base unit having a transmission module that is configured to send at least one or more of the sensed data and the movement data to a remote computing device.

15. The system of claim 14, wherein the base unit has a defibrillator that is configured to deliver defibrillation to the patient.

16. The system of claim 14, wherein the base unit has one or more of a global positioning system, a landline connection, and a cellular connection.

17. The system of claim 14, wherein the base unit further includes a power supply configured to supply power to the one or more sensors, the processing unit, and the at least one feedback component.

18. The system of claim 14, wherein at least one of the processing unit and the at least one feedback component are positioned on the wearable article.

19. A system, comprising:
a wearable cardiopulmonary resuscitation assist device that includes:
a wearable article configured to be selectively attached around a torso of a patient;
one or more sensors housed in the wearable article and configured to be in physical contact with the patient when the wearable article is attached around the torso of the patient and a performer is administering cardiopulmonary resuscitation to the patient, the one or more sensors including at least one accelerometer that is configured to sense multiple of a position, an angle, or a movement of at least two of a chest of the patient, an arm of the performer, and a hand of the performer while the cardiopulmonary resuscitation is being administered to the patient, the one or more sensors configured to generate sensed data that is based at least in part on the multiple of the position, the angle, or the movement of the at least two of the chest of the patient, the arm of the performer, and the hand of the performer;
a base unit having:
a processing unit configured to receive the sensed data from the one or more sensors
and to generate movement data based at least in part on the received, sensed data; and
at least one feedback component configured to receive the movement data and convey the movement data to an output.

20. The system of claim 19, wherein the base unit has a transmission module configured to send one or both of the sensed data and the movement data to a remote computing system.

21. A wearable medical device, comprising:
a wearable article configured to be selectively attached around a torso of a patient;
at least one ECG sensor housed in the wearable article and configured to be in physical contact with the patient when the wearable article is attached around the torso of the patient,
one or more sensors housed in the wearable article and configured to be in physical contact with the patient when the wearable article is attached around the torso of the patient and a performer is administering cardiopulmonary resuscitation to the patient, the one or more sensors including at least one accelerometer that is configured to sense multiple of a position, an angle, or a movement of at least two of a chest of the patient, an arm of the performer, and a hand of the performer while the cardiopulmonary resuscitation is being administered to the patient, the one or more sensors configured to generate sensed data that is based at least in part on the multiple of the position, the angle, or the movement of the at least two of the chest of the patient, the arm of the performer, and the hand of the performer;
a processing unit configured to receive the sensed data from the one or more sensors and to generate processed data based at least in part on the received, sensed data; and
a transmission module configured to send one or both of the sensed data and the processed data to a remote computing system.

22. The device of claim 21, wherein the device also has a base unit configured to be in communication with one or both of the at least one ECG sensor and the at least one accelerometer, the base unit including the transmission module that is configured to send one or more of data sensed by the ECG sensor, the processed data, and the movement data sensed by the accelerometer to the remote computing system.

23. The system of claim 22, wherein the base unit has one or more of a global positioning system, a landline connection, and a cellular connection.

24. The system of claim 21, wherein the base unit further includes a power supply configured to supply power to one or more of the ECG sensor and the accelerometer, and the processing unit.

* * * * *